US009540340B2

(12) United States Patent
DeWitt

(10) Patent No.: US 9,540,340 B2
(45) Date of Patent: Jan. 10, 2017

(54) 3-(5-SUBSTITUTED-4-OXOQUINAZOLIN-3(4H)-YL)-3-DEUTERO-PIPERIDINE-2,6-DIONE DERIVATIVES AND COMPOSITIONS COMPRISING AND METHODS OF USING THE SAME

(71) Applicant: DeuteRx, LLC, Andover, MA (US)

(72) Inventor: Sheila DeWitt, Auburn, NH (US)

(73) Assignee: DeuteRx, LLC, Andover, MA (US)

( * ) Notice: Subject to any disclaimer, the term of this patent is extended or adjusted under 35 U.S.C. 154(b) by 0 days.

(21) Appl. No.: 14/154,743

(22) Filed: Jan. 14, 2014

(65) Prior Publication Data

US 2014/0228382 A1 Aug. 14, 2014

Related U.S. Application Data

(60) Provisional application No. 61/786,024, filed on Mar. 14, 2013, provisional application No. 61/752,055, filed on Jan. 14, 2013.

(51) Int. Cl.
*C07D 401/04* (2006.01)

(52) U.S. Cl.
CPC .................... *C07D 401/04* (2013.01)

(58) Field of Classification Search
CPC .................................................. C07D 401/04
USPC .................................... 514/266.22; 544/287
See application file for complete search history.

(56) References Cited

U.S. PATENT DOCUMENTS

| | | | |
|---|---|---|---|
| 4,421,865 A | 12/1983 | Shen | |
| 5,149,820 A | 9/1992 | Borretzen et al. | |
| 5,635,517 A | 6/1997 | Muller et al. | |
| 5,955,476 A | 9/1999 | Muller et al. | |
| 6,221,335 B1 | 4/2001 | Foster | |
| 6,334,997 B1 | 1/2002 | Foster et al. | |
| 6,440,710 B1 | 8/2002 | Keinan et al. | |
| 6,603,008 B1 | 8/2003 | Ando et al. | |
| 7,091,353 B2 | 8/2006 | Robarge et al. | |
| 7,189,740 B2 | 3/2007 | Zeldis | |
| 7,393,863 B2 | 7/2008 | Zeldis | |
| 7,459,466 B2 | 12/2008 | Muller et al. | |
| 7,465,800 B2 | 12/2008 | Jaworsky et al. | |
| 7,517,990 B2 | 4/2009 | Ito et al. | |
| 7,576,104 B2 | 8/2009 | Robarge et al. | |
| 7,635,700 B2 | 12/2009 | Muller et al. | |
| 7,820,697 B2 | 10/2010 | Man et al. | |
| 8,012,997 B2 | 9/2011 | Robarge et al. | |
| 8,153,659 B2 | 4/2012 | Ruchelman et al. | |
| 8,288,414 B2 | 10/2012 | Czarnik | |
| 8,288,537 B2 | 10/2012 | Golec et al. | |
| 8,481,568 B2 | 7/2013 | Muller et al. | |
| 8,492,395 B2 | 7/2013 | Muller et al. | |
| 8,518,972 B2 | 8/2013 | Man et al. | |
| 8,669,276 B2 | 3/2014 | Czarnik | |
| 9,090,585 B2 | 7/2015 | DeWitt | |
| 9,290,475 B2 | 3/2016 | DeWitt | |
| 2003/0096841 A1 | 5/2003 | Robarge et al. | |
| 2007/0004920 A1 | 1/2007 | Ge et al. | |
| 2007/0049618 A1 | 3/2007 | Muller et al. | |
| 2007/0066512 A1 | 3/2007 | Verhelle et al. | |
| 2007/0082929 A1 | 4/2007 | Gant et al. | |
| 2007/0197695 A1 | 8/2007 | Potyen et al. | |
| 2008/0199422 A1 | 8/2008 | Zeldis | |
| 2009/0022706 A1 | 1/2009 | Gant et al. | |
| 2009/0054433 A1 | 2/2009 | Nam et al. | |
| 2009/0069379 A1 | 3/2009 | Czarnik | |
| 2009/0082375 A1 | 3/2009 | Cameron et al. | |
| 2009/0093504 A1 | 4/2009 | Muller et al. | |
| 2009/0317385 A1 | 12/2009 | Brady et al. | |
| 2010/0016342 A9 | 1/2010 | Cameron et al. | |
| 2011/0196150 A1 | 8/2011 | Man et al. | |
| 2012/0230982 A1 | 9/2012 | Zhou et al. | |
| 2012/0232100 A1 | 9/2012 | Muller et al. | |
| 2012/0252844 A1 | 10/2012 | DeWitt | |
| 2012/0302605 A1 | 11/2012 | DeWitt | |
| 2012/0322073 A1 | 12/2012 | Lopez-Girona et al. | |
| 2012/0322799 A1 | 12/2012 | Damodara | |
| 2013/0274291 A1 | 10/2013 | Dewitt | |
| 2014/0142141 A1 | 5/2014 | Czarnik | |
| 2014/0288101 A1 | 9/2014 | DeWitt | |
| 2015/0203469 A1* | 7/2015 | Man .................... C07D 401/04 514/266.22 |
| 2015/0361066 A1 | 12/2015 | Traverse | |
| 2016/0002202 A1 | 1/2016 | DeWitt | |

FOREIGN PATENT DOCUMENTS

| | | |
|---|---|---|
| WO | WO-95/26325 A2 | 10/1995 |
| WO | WO-95/26325 A3 | 12/1995 |
| WO | WO-99/47512 A1 | 9/1999 |
| WO | WO-02/059106 A1 | 8/2002 |

(Continued)

OTHER PUBLICATIONS

U.S. Appl. No. 17/211,889, filed Mar. 14, 2014.*
CoNCERT Pharmaceuticals, Inc. (2007) "Precisional Deuterium Chemistry Backgrounder," 6 pages.
Extended European Search Report for EP 12764895 dated Oct. 17, 2014 (9 pages).
Buteau, K., "Deuterated Drugs: Unexpectedly Nonobvious?", 10 J. High Tech. L. 22 (2009).
Chemical Database Search Results, 3 pages (2011).
Foster, A., "Deuterium isotope effects in studies of drug metabolism", TIPS, Dec. 1984, 524-527.
Foster, A., "Deuterium Isotope Effects in the Metabolism of Drugs and Xenobiotics: Implications for Drug Design", Adv. Drug Res., 14:2-40 (1985).
Harbeson et al., "Deuterium in Drug Discovery and Development", Annual Reports in Med Chem, 46:403-417 (2011).
Hutt et al., "The Chiral Switch: The Development of Single Enantiomer Drugs from Racemates", ACTA Facult. Pharm. Univ. Comenianae, 50:7-23 (2003).
International Search Report and Written Opinion for PCT/US12/30870 dated Jul. 9, 2012 (corresponding PCT application).
International Search Report and Written Opinion for PCT/US2011/061485 dated Apr. 5, 2012.
International Search Report and Written Opinion for PCT/US2014/011440 dated Apr. 25, 2014.
International Search Report and Written Opinion for PCT/US2014/027918 dated Jul. 28, 2014.
Kaufman et al., "Deuterium Enrichment of Vitamin A at the C20 Position Slows the Formation of Detrimental Vitamin A Dimers in Wild-type Rodents", J. Biol. Chem., 286(10):7958-7965 (2011).

(Continued)

*Primary Examiner* — Paul V Ward
(74) *Attorney, Agent, or Firm* — Goodwin Procter LLP

(57) ABSTRACT

The invention provides 3-deuterium-enriched 3-(5-substituted-4-oxoquinazolin-3(4H)-yl)-piperidine-2,6-diones, deuterated derivatives thereof, stereoisomers thereof, pharmaceutically acceptable salt forms thereof, and methods of treatment using the same, such as in the treatment of cancer, an immune-related disease, or an inflammatory disease.

4 Claims, 10 Drawing Sheets

(56) References Cited

FOREIGN PATENT DOCUMENTS

| WO | WO-02/094180 A2 | 11/2002 |
|---|---|---|
| WO | WO-2006/053160 A2 | 5/2006 |
| WO | WO-2006/127938 A1 | 11/2006 |
| WO | WO-2007/027527 A2 | 3/2007 |
| WO | WO-2007/136640 A2 | 11/2007 |
| WO | WO-2008/027542 A2 | 3/2008 |
| WO | WO-2008/033567 A1 | 3/2008 |
| WO | WO-2008/039489 A2 | 4/2008 |
| WO | WO-2008/115516 A2 | 9/2008 |
| WO | WO-2009/042177 A1 | 4/2009 |
| WO | WO-2009/042200 A1 | 4/2009 |
| WO | WO-2009/085234 A9 | 7/2009 |
| WO | WO-2009/097120 A1 | 8/2009 |
| WO | WO-2009/105256 A2 | 8/2009 |
| WO | WO-2009/139880 A1 | 11/2009 |
| WO | WO-2009/145899 A1 | 12/2009 |
| WO | WO-2010/053732 A1 | 5/2010 |
| WO | WO-2010/056344 A1 | 5/2010 |
| WO | WO-2010/093434 A1 | 8/2010 |
| WO | WO-2010/093605 A1 | 8/2010 |
| WO | WO-2009/105256 A3 | 11/2010 |
| WO | WO-2011/079091 A1 | 6/2011 |
| WO | WO-2011/100380 A1 | 8/2011 |
| WO | WO-2012/015986 | 2/2012 |
| WO | WO-2012/027065 A2 | 3/2012 |
| WO | WO-2012/068512 A1 | 5/2012 |
| WO | WO-2012/079022 | 6/2012 |
| WO | WO-2012/125438 A1 | 9/2012 |
| WO | WO-2012/125459 A1 | 9/2012 |
| WO | WO-2012/125475 A1 | 9/2012 |
| WO | WO-2012/135299 A1 | 10/2012 |
| WO | WO-2012/149299 A2 | 11/2012 |
| WO | WO-2014/004990 A2 | 1/2014 |
| WO | WO-2014/025958 A2 | 2/2014 |
| WO | WO-2014/025964 A2 | 2/2014 |
| WO | WO-2014/025978 A1 | 2/2014 |
| WO | WO-2014/039421 A1 | 3/2014 |
| WO | WO-2014/039960 A1 | 3/2014 |
| WO | WO-2014/110558 A1 | 7/2014 |
| WO | WO-2014/152833 A1 | 9/2014 |

OTHER PUBLICATIONS

Maltais et al., "In Vitro and In Vivo Isotope Effects with Hepatitis C Protease Inhibitors: Enchanced Plasma Exposure of Deuterated Telaprevir versus Telaprevir in Rats", J. Med. Chem., 52:7993-8001 (2009).
Man et al., "α-Fluoro-Substituted Thalidomide Analogues", Bioorg. Med. Chem. Ltrs. 13:3415-3417 (2003).
Mislow et al., "A Note on Steric Isotope Effects. Conformational Kinetic Isotope Effects in the Racemization of 9,10-Dihydro-4,5-Dimethylphenanthrene", JACS, 85:1199-1200 (1963).
Nassar et al., "Improving the decision-making process in the structural modification of drug candidates: enhancing metabolic stability", DDT, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", DMD, 31(12):1481-1498 (2003).
Shao et al., "Derivatives of tramadol for increased duration of effect", Bioorg. Med. Chem. Lett. 16:691-694 (2006).
Shao et al., "The Kinetic Isotope Effect in the Search for Deuterated Drugs", Drug News & Perspectives, 23(6):398-404 (2010).
Stedman et al., "Review article: comparison of the pharmacokinetics, acid suppression and efficacy of proton pump inhibitors", Aliment Pharmacol. Ther., 14:963-978 (2000).
Takeuchi et al., "(R)- and (S)-3-Fluorothalidomides: Isosteric Analogues of Thalidomide", Organic Ltrs. 1(10):1571-1573 (1999).
Teo et al., "Chiral inversion of the second generation IMiD™ CC-4047 (ACTIMID™) in human plasma and phosphate-buffered saline", *Chirality*, 2003, 15(4), 348-351 (Abstract).
Wiberg, K., "The Deuterium Isotope Effect", Chem. Rev., 55(4):713-743 (1955).
Yamamoto et al., "Synthesis and Configurational Stability of (S)- and (R)- Deuteriothalidomides", Chem. Pharm. Bull. 58(1):110-112 (2010).
Yarnell, A., "Heavy-Hydrogen Drugs Turn Heads, Again", Chemical & Engineering News, 87(25):36-39 (2009).
Zhu et al., "Deuterated Clopidogrel Analogues as a New Generation of Antiplatelet Agents", ACS Med. Chem. Lett., (2013) (4 pages).
Chen et al., "Pharmacokinetics, metabolism and excretion of [$^{14}$C]-lenalidomide following oral administration in healthy male subjects," Cancer Chemother Pharmacol, vol. 69, pp. 789-797 (2012).
Hoffman et al., "Absorption, metabolism and excretion of [$^{14}$C]pomalidomide in humans following oral administration," *Cancer Chemother Pharmacol*, vol. 71, pp. 489-501 (2013).
Distler et al., "CC-220: A Clinical Stage Immunomodulatory, Antifibrotic Drug for Systemic Sclerosis" at American College of Rheumatology/Association of Rheumatology Health Professionals Annual Meeting, (2013).
Distler et al., "CC-220: A Clinical Stage Immunomodulatory, Antifibrotic Drug For Systemic Sclerosis," Arthritis Rheumatism, vol. 65, (2013). Abstract only.
Schafer et al., "The CUL4 E3 Ubiquitin Ligase Modulator CC-220 Induces Degradation of the Transcription Factors Ikaros and Aiolos: Immunomodulation in Healthy Volunteers and Relevance to Systemic Lupus Erythematosus," American College of Rheumatology Meeting, (2014).
Fisher et al., "The complexities inherent in attempts to decrease drug clearance by blocking sites of CYP-mediated metabolism", Curr. Opin. Drug Disc. Dev., 9(1):101-109 (2006).
Blake et al., "Studies with Deuterated Drugs", J. Phar. Sci., 64(3):367-391 (1975).
Dörwald, F., "Side Reactions in Organic Synthesis: A Guide to Successful Synthesis Design", Wiley-VCH, p. ix (2005).
Wade, D., "Deuterium isotope effects on noncovalent interactions between molecules", Chemico-Biological Interactions, 117 p. 191-217 (1999).
McMahon, G., "VEGF Receptor Signaling in Tumor Angiogenesis", The Oncologist, 5(suppl 1):3-10 (2000).
Pinedo et al., "Translational Research: The Role of VEGF in Tumor Angiogenesis", The Oncologist, 5(suppl 1):1-2 (2000).

\* cited by examiner

US 9,540,340 B2

3-(5-SUBSTITUTED-4-OXOQUINAZOLIN-3(4H)-YL)-3-DEUTERO-PIPERIDINE-2,6-DIONE DERIVATIVES AND COMPOSITIONS COMPRISING AND METHODS OF USING THE SAME

RELATED APPLICATIONS

This application claims the benefit of and priority to U.S. Provisional Patent Application Ser. No. 61/752,055, filed Jan. 14, 2013, and U.S. Provisional Patent Application Ser. No. 61/786,024, filed Mar. 14, 2013; the contents of each of which are hereby incorporated by reference.

BACKGROUND

Compounds such as 3-(5-amino-2-methyl-4-oxoquinazolin-3(4H)-yl)-piperidine-2,6-dione (Formula A) and 3-(2,5-di-methyl-4-oxoquinazolin-3(4H)-yl)-piperidine-2,6-dione (Formula B) and other derivatives in this family are currently being studied as anti-proliferative, immunomodulatory, and anti-angiogenic agents.

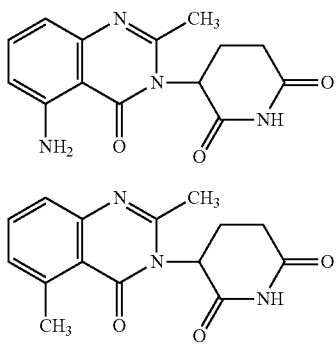

The above compounds are described in U.S. Pat. Nos. 7,635,700 and 8,492,395; U.S. Patent Application Publication Nos. 2009/0082375, 2010/0016342, 2012/0230982, and 2012/0232100; and International Patent Application Publication No. WO 2012/125475; the contents of which are hereby incorporated by reference.

The compounds of Formula A and B, because of the asymmetric carbon on the glutarimide ring (i.e., the piperidine-2,6-dione ring), are a racemic mixture of R and S stereoisomers. The hydrogen at the 3-position is acidic due to the presence of the adjacent carbonyl moiety, thereby making it difficult to prevent racemization of the two stereoisomers and difficult to determine if one of the stereoisomers is superior to the other.

The present invention provides new compounds that are resistant to racemization at their stereogenic center, and are useful in the treatment of various medical disorders.

SUMMARY OF THE INVENTION

Accordingly, described herein are 3-deuterium-enriched 3-(5-substituted-4-oxoquinazolin-3(4H)-yl)-piperidine-2,6-diones (e.g., 3-(5-substituted-4-oxoquinazolin-3(4H)-yl)-3-deutero-piperidine-2,6-diones) and stereoisomers, solvates, and pharmaceutically acceptable salts thereof.

Another aspect provided herein is a pharmaceutical composition comprising a pharmaceutically acceptable carrier and at least one of the deuterium-enriched compounds of the invention or a stereoisomer, solvate, or pharmaceutically acceptable salt thereof.

Another aspect is a method for treating, preventing, and/or managing angiogenesis and/or a cytokine related disorder, comprising administering to a host in need of such treatment a therapeutically effective amount of at least one of the deutero-compounds of the invention or a stereoisomer, solvate, or pharmaceutically acceptable salt thereof.

Another aspect is a method for treating, preventing, and/or managing a cancer, comprising administering to a host in need of such treatment a therapeutically effective amount of at least one of the deutero-compounds of the invention or a stereoisomer, solvate, or pharmaceutically acceptable salt thereof.

Another aspect is a method for treating, preventing, and/or managing a disease associated with lymphocytic activity, including activity of B cells and/or T cells, e.g., immune-related diseases or inflammatory diseases, comprising administering to a host in need of such treatment a therapeutically effective amount of at least one of the deutero-compounds of the invention or a stereoisomer, solvate, or pharmaceutically acceptable salt thereof.

Also provided are novel 3-deuterium-enriched 3-(5-substituted-4-oxoquinazolin-3(4H)-yl)-piperidine-2,6-diones or a stereoisomer, solvate, or pharmaceutically acceptable salt thereof for use in therapy.

Another aspect is the use of novel 3-deuterium-enriched 3-(5-substituted-4-oxoquinazolin-3(4H)-yl)-piperidine-2,6-diones or a stereoisomer, solvate, or pharmaceutically acceptable salt thereof for the manufacture of a medicament (e.g., for the treatment of angiogenesis and/or a cytokine related disorder). In certain instances, the treatment is for cancer, an immune-related disease, or an inflammatory disease.

These and other aspects, which will become apparent during the following detailed description, have been achieved by the inventor's discovery of 3-deuterium-enriched 3-(5-substituted-4-oxoquinazolin-3 (4H)-yl)-piperidine-2,6-diones.

DETAILED DESCRIPTION

Figure 1:
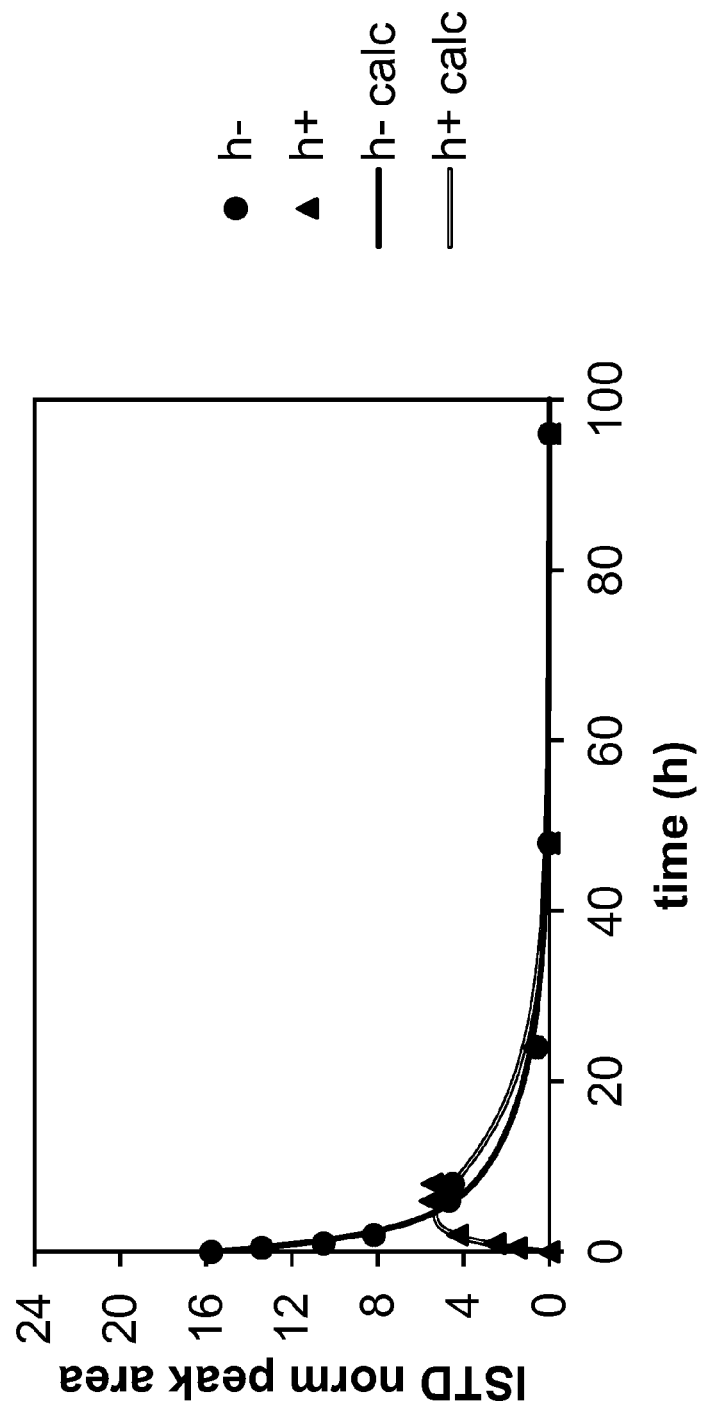
FIG. 1 is a graph showing in vitro stability data for (−)-3-(5-amino-2-methyl-4-oxoquinazolin-3(4H)-yl)-piperidine-2,6-dione (designated "h-") in human plasma, as described in Example 3, where the abbreviation "calc" indicates results from fitting experimental data to kinetic differential equations.

Deuterium (D or $^2$H) is a stable, non-radioactive isotope of hydrogen and has an atomic weight of 2.014. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts. Thus, the present invention relates to a deuterium-enriched compound or compounds whose enrichment is greater than naturally occurring deuterated molecules.

All percentages given for the amount of deuterium present are mole percentages. Further, when a variable is not accompanied by a definition, the previous definition of the variable controls.

Unless indicated otherwise, when a D is specifically recited at a position or is shown in a formula, this D represents a mixture of hydrogen and deuterium where the amount of deuterium is about 100% (i.e., the abundance of deuterium is from 90% to 100%). In certain aspects, the abundance of deuterium is from 97% to 100%).

The 3-deuterium group (i.e., the Z group) in the present compounds means that the compounds have been isotopically enriched at the 3-position and are different and distinct from the corresponding non-enriched compound.

Compound refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

I. EXEMPLARY DEUTERIUM-ENRICHED COMPOUNDS

One aspect of the invention provides a deuterium-enriched compound of Formula I:

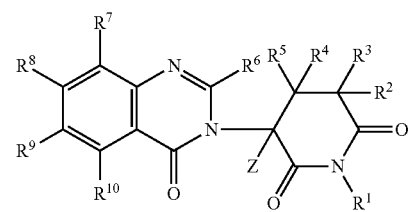

and pharmaceutically acceptable salts, solvates, and stereoisomers thereof, wherein:

Z is H or D, provided that the abundance of deuterium in Z is at least 30%;

$R^1$, $R^2$, $R^3$, $R^4$, $R^5$, $R^7$, $R^8$, and $R^9$ are independently selected from H and D;

$R^6$ is selected from: H; D; —(CH$_2$)$_n$OH; phenyl; —O(C$_1$-C$_6$)alkyl; and (C$_1$-C$_6$)alkyl optionally substituted with one or more halo;

$R^{10}$ is selected from: H; D; halo; —(CH$_2$)$_n$OH; (C$_1$-C$_6$) alkyl optionally substituted with one or more halo; (C$_1$-C$_6$) alkoxy optionally substituted with one or more halo; and —(CH$_2$)$_n$NHR$^a$;

$R^a$ is selected from: H; D; (C$_1$-C$_6$)alkyl optionally substituted with one or more halo; —(CH$_2$)$_n$-(6 to 10 membered aryl); —C(O)(CH$_2$)$_n$-(6 to 10 membered aryl); —C(O)(CH$_2$)$_n$-(6 to 10 membered heteroaryl); —C(O)(C$_1$-C$_8$)alkyl optionally substituted with one or more halo; —C(O)(CH$_2$)$_n$—(C$_3$-C$_{10}$-cycloalkyl); —C(O)(CH$_2$)$_n$—NR$^b$R$^c$; —C(O) (CH$_2$)$_n$—O—(C$_1$-C$_6$)alkyl; and, —C(O)(CH$_2$)$_n$—O—(CH$_2$)$_n$-(6 to 10 membered aryl); wherein the aryl and heteroaryl are optionally substituted with one or more groups selected from: halo; —SCF$_3$; (C$_1$-C$_6$)alkyl optionally substituted with one or more halo; and (C$_1$-C$_6$)alkoxy optionally substituted with one or more halo;

$R^b$ and $R^c$ are each independently selected from: H; D; (C$_1$-C$_6$)alkyl optionally substituted with one or more halo;

($C_1$-$C_6$)alkoxy optionally substituted with one or more halo; and 6 to 10 membered aryl; the aryl being optionally substituted with one or more groups selected from: halo; ($C_1$-$C_6$)alkyl optionally substituted with one or more halo; and ($C_1$-$C_6$)alkoxy optionally substituted with one or more halo;

alternatively, $R^{10}$ is selected from $R^{10a}$, $R^{10b}$, $R^{10c}$;

$R^{10a}$ is selected from: H; D; halo; —$(CH_2)_n$OH; ($C_1$-$C_6$) alkyl optionally substituted with one or more halo; and ($C_1$-$C_6$)alkoxy optionally substituted with one or more halo;

$R^{10b}$=—$(CH_2)_n$—$NHR^d$;

$R^{10c}$=—$(CH_2)_n$—$NHR^g$;

$R^d$ is selected from: H; D; —($C_1$-$C_6$)alkyl optionally substituted with one or more halo; —C(O)($C_1$-$C_8$)alkyl optionally substituted with one or more halo; —C(O)($CH_2)_n$ ($C_3$-$C_{10}$-cycloalkyl); —C(O)($CH_2)_n NR^e R^f$; and, —C(O)($CH_2)_n O(C_1$-$C_6$)alkyl.

$R^e$ and $R^f$ are each independently selected from: hydrogen; ($C_1$-$C_6$)alkyl optionally substituted with one or more halo; and ($C_1$-$C_6$)alkoxy optionally substituted with one or more halo;

$R^g$ is selected from: —C(O)($CH_2)_n$—$NHR^h$; —$(CH_2)_n$-(6 to 10 membered aryl); —C(O)($CH_2)_n$-(6 to 10 membered aryl); —C(O)($CH_2)_n$-(6 to 10 membered heteroaryl); and, —C(O)($CH_2)_n O(CH_2)_n$-(6 to 10 membered aryl), wherein the aryl and heteroaryl are optionally substituted with one or more groups selected from: halo; —$SCF_3$; ($C_1$-$C_6$)alkyl optionally substituted with one or more halo; and, ($C_1$-$C_6$) alkoxy substituted with one or more halo;

$R^h$ is selected from: 6 to 10 membered aryl optionally substituted with one or more groups selected from: halo; ($C_1$-$C_6$)alkyl optionally substituted with one or more halo; and, ($C_1$-$C_6$)alkoxy optionally substituted with one or more halo;

n is independently selected from selected from 0, 1, and 2; and a hydrogen atom present in any substituent is optionally replaced by D.

In another aspect, n is 0. In another aspect, n is 1. In another aspect, n is 2.

In certain embodiments, the compound is a compound of Formula I or a pharmaceutically acceptable salt or stereoisomer thereof.

Another aspect of the invention provides a deuterium-enriched compound of Formula I-A:

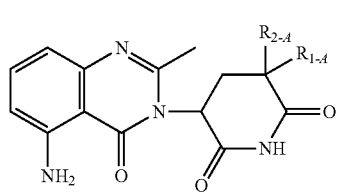

I-A and pharmaceutically acceptable salts and stereoisomers thereof, wherein:

Z is H or D, provided that the abundance of deuterium in Z is at least 30%;

$R_{1-A}$ and $R_{2-A}$ are independently selected from H and D.

In certain embodiments, $R_{1-A}$ and $R_{2-A}$ are H. In certain embodiments, the compound is the (−)-enantiomer. In certain other embodiments, the compound is the (+)-enantiomer.

In certain embodiments, the deuterium-enriched compound is one of the generic formulae described herein wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

Deuterium-enriched compounds characterized according to their stereochemical purity are provided. The stereochemical purity of compounds having one stereocenter can be characterized as enantiomeric excess (ee). Enantiomeric excess can be calculated using the formula:

$$ee(\%) = (R-S)/(R+S)*100$$

where R and S are the amounts of (R) and (S) enantiomers in the mixture.

For compounds having two or more stereocenters, the stereochemical purity (sp) refers to the percentage of 1 of the 4 or more possible stereoisomers being present. For a compound with two stereocenters, the stereomeric purity can be calculated using the formula:

$$sp(\%)=\% \text{ Isomer } 1-(\% \text{ Isomer } 2+\% \text{ Isomer } 3+\% \text{ Isomer } 4)$$

where % Isomer # is the weight (e.g., mole) % of one of the isomers in the mixture.

In another aspect, the present invention provides a compound having an enantiomeric excess, with respect to the C—Z carbon, of at least 5%. Exantiomeric excess, with respect to the C—Z carbon (i.e., 3-carbon of the glutarimide), refers only to the stereomeric purity around this carbon, regardless of whether or not additional stereocenters are present in the compound.

In another aspect, the present invention provides deuterium-enriched compounds wherein the enantiomeric excess is selected from: (a) at least 10%, (b) at least 20%, (c) at least 30%, (d) at least 40%, (e) at least 50%, (f) at least 60%, (g) at least 70%, (h) at least 80%, (i) at least 90%, (j) at least 95%, (k) at least 97%, (l) at least 98%, and (m) at least 99%. Additional examples of the stereoisomeric purity include an enantiomeric excess of at least 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In another aspect, the present invention provides a compound having stereomeric purity of at least 5%.

In another aspect, the present invention provides deuterium-enriched compounds wherein the stereomeric purity is selected from: (a) at least 10%, (b) at least 20%, (c) at least 30%, (d) at least 40%, (e) at least 50%, (f) at least 60%, (g) at least 70%, (h) at least 80%, (i) at least 90%, (j) at least 95%, (k) at least 97%, (l) at least 98%, and (m) at least 99%. Additional examples of the stereoisomeric purity include at least 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In yet other embodiments, the deuterium-enriched compound is a compound of Formula I-B:

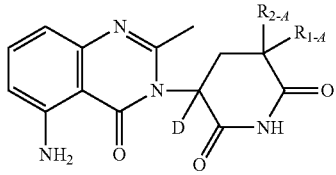

(I-B)

and pharmaceutically acceptable salts and stereoisomers thereof, wherein $R_{1-A}$ and $R_{2-A}$ are independently selected from H and D.

In certain embodiments, $R_{1-A}$ and $R_{2-A}$ are H. In certain embodiments, the compound is the (−)-enantiomer. In certain other embodiments, the compound is the (+)-enantiomer.

In yet other embodiments, the deuterium-enriched compound is a compound of Formula I-C:

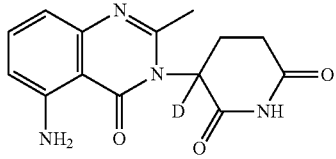

(I-C)

and pharmaceutically acceptable salts and stereoisomers thereof.

In certain embodiments, the compound is the (−)-enantiomer. In certain other embodiments, the compound is the (+)-enantiomer.

In yet other embodiments, the deuterium-enriched compound is a compound of Formula I-D having an optical purity of at least 75% enantiomeric excess:

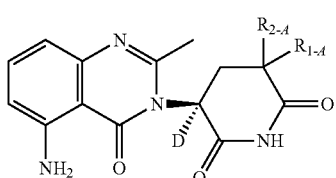

(I-D)

and pharmaceutically acceptable salts thereof, wherein $R_{1-A}$ and $R_{2-A}$ are independently selected from H and D.

In certain embodiments, $R_{1-A}$ and $R_{2-A}$ are H. In certain embodiments, the compound has an optical purity of at least 85% enantiomeric excess, 90% enantiomeric excess, 95% enantiomeric excess, or 98% enantiomeric excess.

In yet other embodiments, the deuterium-enriched compound is a compound of Formula I-E having an optical purity of at least 75% enantiomeric excess:

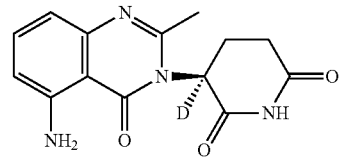

(I-E)

and pharmaceutically acceptable salts thereof.

In certain embodiments, the compound has an optical purity of at least 85% enantiomeric excess, 90% enantiomeric excess, 95% enantiomeric excess, or 98% enantiomeric excess.

In yet other embodiments, the deuterium-enriched compound is a compound of Formula I-F having an optical purity of at least 75% enantiomeric excess:

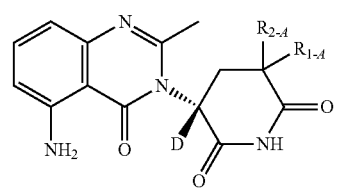

(I-F)

and pharmaceutically acceptable salts thereof, wherein $R_{1-A}$ and $R_{2-A}$ are independently selected from H and D.

In certain embodiments, $R_{1-A}$ and $R_{2-A}$ are H. In certain embodiments, the compound has an optical purity of at least 85% enantiomeric excess, 90% enantiomeric excess, 95% enantiomeric excess, or 98% enantiomeric excess.

In yet other embodiments, the deuterium-enriched compound is a compound of Formula I-G having an optical purity of at least 75% enantiomeric excess:

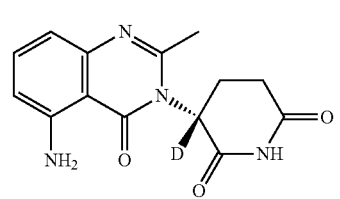

(I-G)

and pharmaceutically acceptable salts thereof.

In certain embodiments, the compound has an optical purity of at least 85% enantiomeric excess, 90% enantiomeric excess, 95% enantiomeric excess, or 98% enantiomeric excess.

In another aspect, the present invention provides deuterium-enriched compounds of formula Ia or Ib:

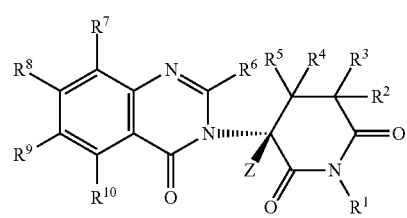

Ia

-continued

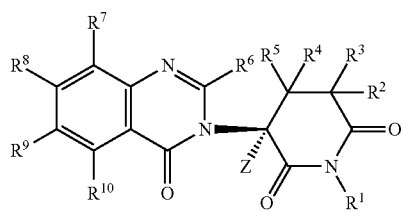
Ib and pharmaceutically acceptable salts and solvates thereof, wherein Z, $R^1$, $R^2$, $R^3$, $R^4$, $R^5$, $R^6$, $R^7$, $R^8$, $R^9$, and $R^{10}$ are as defined above for formula I.

In another aspect, the present invention provides deuterium-enriched compounds of formula Ia or Ib:

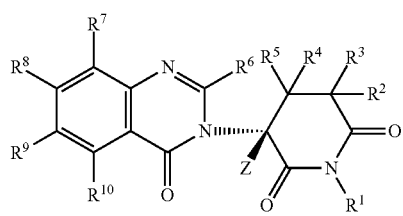
Ia

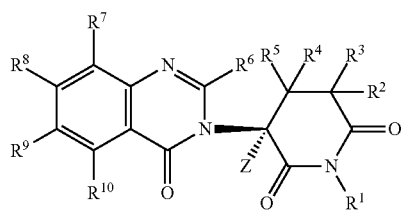
Ib and pharmaceutically acceptable salts and solvates thereof, wherein Z, $R^1$, $R^2$, $R^3$, $R^4$, $R^5$, $R^6$, $R^7$, $R^8$, $R^9$, and $R^{10}$ are as defined above for formula I, and wherein the compound has an enantiomeric excess, with respect to the C—Z carbon, of at least 5%.

In another aspect, the present invention provides deuterium-enriched compounds of formula Ic or Id:

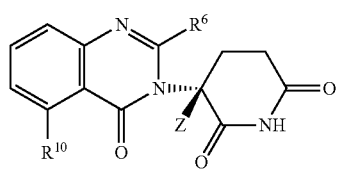
Ic

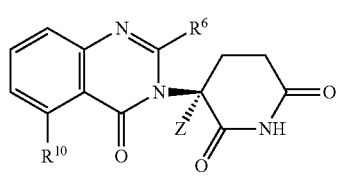
Id and pharmaceutically acceptable salts and solvates thereof, wherein Z, $R^6$, and $R^{10}$ are as defined above for formula I.

In another aspect, the present invention provides deuterium-enriched compounds of formula Ic or Id:

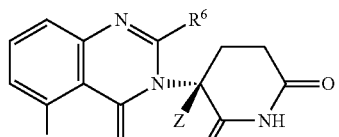
Ic

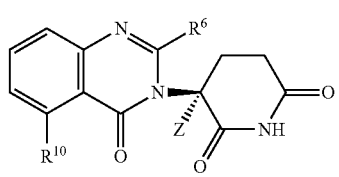
Id and pharmaceutically acceptable salts and solvates thereof, wherein Z, $R^6$, and $R^{10}$ are as defined above for formula I, and wherein the compound has an enantiomeric excess, with respect to the C—Z carbon, of at least 5%.

In another aspect, the present invention provides deuterium-enriched compounds of formula Ie or If:

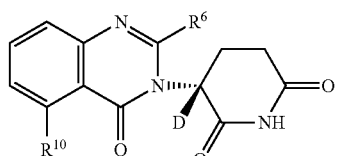
Ie

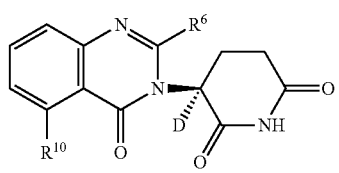
If and pharmaceutically acceptable salts and solvates thereof, wherein $R^6$ and $R^{10}$ are as defined above for formula I.

In another aspect, the present invention provides deuterium-enriched compounds of formula Ie or If:

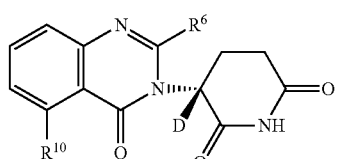
Ie

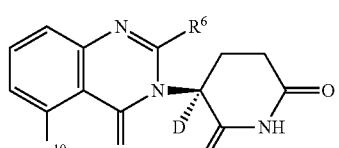
If and pharmaceutically acceptable salts and solvates thereof, wherein $R^6$ and $R^{10}$ are as defined above for formula I, and wherein the compound has an enantiomeric excess, with respect to the C-D carbon, of at least 5%.

In another aspect, the present invention provides deuterium-enriched compounds of formulae Ia-If, wherein $R^{10}=R^{10a}$ (compounds IIa-IIf)), and pharmaceutically acceptable salts and solvates thereof.

In another aspect, $R^{10}=R^{10a}$ and $R^6$ is H.

In another aspect, $R^{10}=R^{10a}$ and $R^6$ is —(CH$_2$)$_n$OH or hydroxyl. In another aspect, $R^{10}=R^{10a}$ and $R^6$ is phenyl. In another aspect, $R^{10}=R^{10}$ and $R^6$ is —O(C$_1$-C$_6$)alkyl optionally substituted with one or more halo.

In another aspect, $R^{10}=R^{10a}$ and $R^6$ is (C$_1$-C$_6$)alkyl optionally substituted with one or more halo.

In another aspect, $R^{10}=R^{10a}$ and $R^6$ is methyl. In another aspect, $R^{10}=R^{10a}$ and $R^6$ is —CF$_3$.

In another aspect, $R^{10}$ is 1H. In another aspect, $R^{10a}$ is halo.

In another aspect, $R^{10a}$ is (C$_1$-C$_6$)alkyl optionally substituted with one or more halo.

In another aspect, $R^{10a}$ is —(CH$_2$)$_n$OH or hydroxyl.

In another aspect, $R^{10a}$ is (C$_1$-C$_6$)alkoxy optionally substituted with one or more halo.

In another aspect, $R^{10a}$ is methyl. In another aspect, $R^{10a}$ is methoxy. In another aspect, $R^{10a}$ is —CF$_3$. In another aspect, $R^{10a}$ is F or Cl.

In another aspect, the present invention provides deuterium-enriched compounds of formulae IIa or IIb:

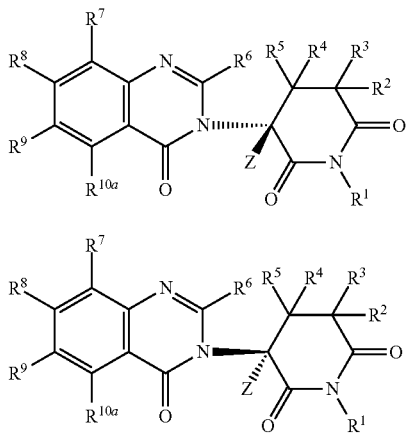

IIa

IIb wherein the compound is selected from:
a. $R^{10a}$=CH$_3$ and $R^6$=H;
b. $R^{10a}$=CH$_3$ and $R^6$=D;
c. $R^{10a}$=CH$_3$ and $R^6$=OH;
d. $R^{10a}$=CH$_3$ and $R^6$=CH$_3$;
e. $R^{10a}$=CH$_3$ and $R^6$=CD$_3$;
f. $R^{10a}$=CH$_3$ and $R^6$=CH$_2$CH$_3$;
g. $R^{10a}$=CH$_3$ and $R^6$=CD$_2$CD$_3$;
h. $R^{10a}$=CH$_3$ and $R^6$=CH$_2$CH$_2$CH$_3$;
i. $R^{10a}$=CH$_3$ and $R^6$=CD$_2$CD$_2$CD$_3$;
j. $R^{10a}$=CH$_3$ and $R^6$=CF$_3$;
k. $R^{10a}$=CH$_3$ and $R^6$=phenyl;
l. $R^{10a}$=CH$_3$ and $R^6$=d$_5$-phenyl;
m. $R^{10a}$=CD$_3$ and $R^6$=H;
n. $R^{10a}$=CD$_3$ and $R^6$=D;
o. $R^{10a}$=CD$_3$ and $R^6$=OH;
p. $R^{10a}$=CD$_3$ and $R^6$=CH$_3$;
q. $R^{10a}$=CD$_3$ and $R^6$=CD$_3$;
r. $R^{10a}$=CD$_3$ and $R^6$=CH$_2$CH$_3$;
s. $R^{10a}$=CD$_3$ and $R^6$=CD$_2$CD$_3$;
t. $R^{10a}$=CD$_3$ and $R^6$=CH$_2$CH$_2$CH$_3$;
u. $R^{10a}$=CD$_3$ and $R^6$=CD$_2$CD$_2$CD$_3$;
v. $R^{10a}$=CD$_3$ and $R^6$=CF$_3$;
w. $R^{10a}$=CD$_3$ and $R^6$=phenyl;
x. $R^{10a}$=CD$_3$ and $R^6$=d$_5$-phenyl;
y. $R^6$=CH$_3$ and $R^{10a}$=OCH$_3$;
z. $R^6$=CH$_3$ and $R^{10a}$=OCD$_3$;
aa. $R^6$=CH$_3$ and $R^{10a}$=F;
bb. $R^6$=CH$_3$ and $R^{10a}$=Cl;
cc. $R^6$=CH$_3$ and $R^{10a}$=CF$_3$;
dd. $R^6$=CD$_3$ and $R^{10a}$=OCH$_3$;
ee. $R^6$=CD$_3$ and $R^{10a}$=OCD$_3$;
ff. $R^6$=CD$_3$ and $R^{10a}$=F;
gg. $R^6$=CD$_3$ and $R^{10a}$=Cl;
hh. $R^6$=CD$_3$ and $R^{10a}$=CF$_3$;
ii. $R^6$=H and $R^{10a}$=Cl; and,
jj. $R^6$=D and $R^{10a}$=Cl.

and pharmaceutically acceptable salts and solvates thereof, wherein:

Z is H or D, provided that the abundance of deuterium in Z is at least 30%;

$R^1$, $R^2$, $R^3$, $R^4$, $R^5$, $R^7$, $R^8$, and $R^9$ are independently selected from H and D; and wherein the compound of formulae IIa or IIb has an enantiomeric excess, with respect to the C—Z carbon, of at least 5%.

In another aspect, the present invention provides deuterium-enriched compounds selected from:

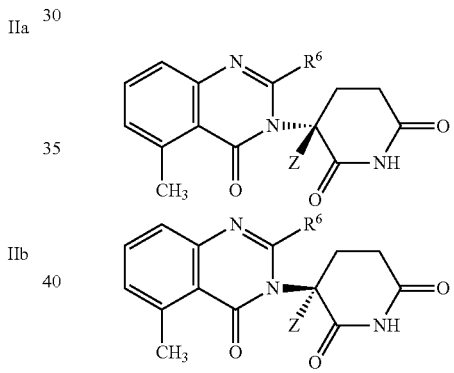

wherein:
a. $R^6$=H;
b. $R^6$=OH;
c. $R^6$=CH$_2$CH$_3$;
d. $R^6$=CH$_2$CH$_2$CH$_3$;
e. $R^6$=CF$_3$;

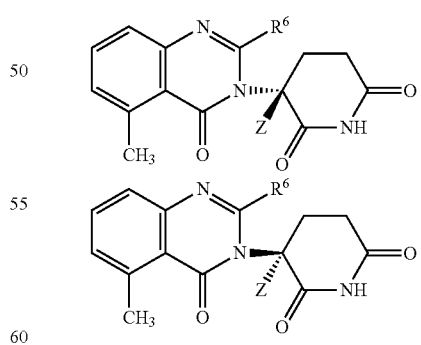

f. $R^6$=phenyl;
g. $R^6$=CH$_3$;

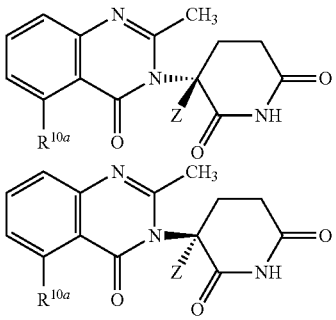

wherein:
h. $R^{10a}$=OCH$_3$;
i. $R^{10a}$=F;
j. $R^{10a}$=Cl;
k. $R^{10a}$=CF$_3$;
l.

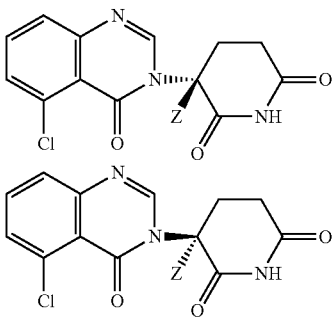

and pharmaceutically acceptable salts and solvates thereof, wherein the compound has an enantiomeric excess, with respect to the C—Z carbon, of at least 5%.

In another aspect, the present invention provides deuterium-enriched compounds of formulae Ia-If, wherein $R^{10}$=$R^{10b}$ (compounds IIIa-IIIf)), and pharmaceutically acceptable salts and solvates thereof.

In another aspect, $R^d$ is H.

In another aspect, $R^d$ is (C$_1$-C$_6$)alkyl optionally substituted with one or more halo.

In another aspect, $R^d$ is —C(O)(C$_1$-C$_8$)alkyl.

In another aspect, $R^d$ is —C(O)(CH$_2$)$_n$(C$_3$-C$_{10}$-cycloalkyl).

In another aspect, $R^d$ is —C(O)(CH$_2$)$_n$NR$^e$R$^f$.

In another aspect, $R^d$ is —C(O)(CH$_2$)$_n$O(CH$_2$)$_n$(C$_1$-C$_6$)alkyl.

In another aspect, $R^d$ is —C(O)(C$_1$-C$_6$)alkyl.

In another aspect, $R^d$ is NH$_2$.

In another aspect, $R^d$ is —C(O)CH$_2$O(C$_1$-C$_6$)alkyl.

In another aspect, $R^{10}$=$R^{10b}$ and $R^6$ is H.

In another aspect, $R^{10}$=$R^{10b}$ and $R^6$ is —(CH$_2$)$_n$OH or hydroxyl.

In another aspect, $R^{10}$=$R^{10b}$ and $R^6$ is phenyl.

In another aspect, $R^{10}$=$R^{10b}$ and $R^6$ is —O(C$_1$-C$_6$)alkyl optionally substituted with one or more halo.

In another aspect, $R^{10}$=$R^{10b}$ and $R^6$ is (C$_1$-C$_6$)alkyl optionally substituted with one or more halo.

In another aspect, $R^{10}$=$R^{10b}$ and $R^6$ is methyl.

In another aspect, the present invention provides deuterium-enriched compounds of formulae IIIa or IIIb:

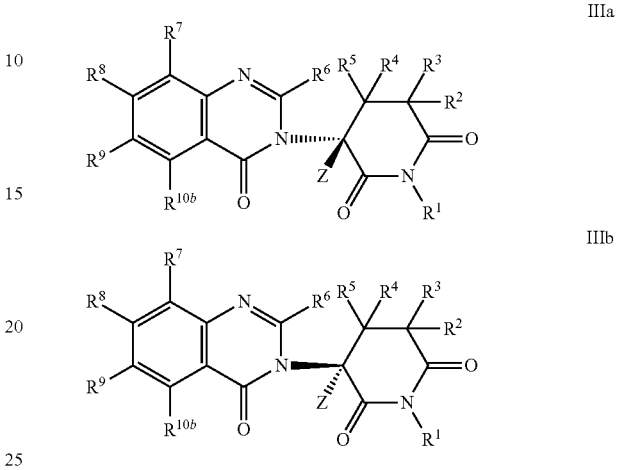

wherein the compound is selected from:
a. $R^6$=CH$_3$ and $R^{10b}$=NH$_2$;
b. $R^6$=CH$_3$ and $R^{10b}$=NHC(O)CH$_2$OCH$_3$;
c. $R^6$=CH$_3$ and $R^{10b}$=NHC(O)CH$_3$;
d. $R^6$=CH$_3$ and $R^{10b}$=NHC(O)-cyclopropyl;
e. $R^6$=CH$_3$ and $R^{10b}$=NHC(O)(CH$_2$)$_5$CH$_3$;
f. $R^6$=CH$_3$ and $R^{10b}$=NHC(O)CH$_2$OCH$_2$CH$_3$;
g. $R^6$=CH$_3$ and $R^{10b}$=NHC(O)CH$_2$N(CH$_3$)$_2$;
h. $R^6$=CH$_3$ and $R^{10b}$=NHC(O)CH$_2$Cl;
i. $R^6$=CH$_3$ and $R^{10b}$=NHC(O)OCH$_2$CH$_3$;
j. $R^6$=CH$_3$ and $R^{10b}$=CH$_2$NHC(O)OC(CH$_3$)$_3$;
k. $R^6$=CH$_3$ and $R^{10b}$=CH$_2$NHC(O)CH$_3$;
l. $R^6$=CH$_3$ and $R^{10b}$=CH$_2$NHC(O)(CH$_2$)$_5$CH$_3$;
m. $R^6$=CH$_3$ and $R^{10b}$=CH$_2$NHC(O)CH$_2$C(CH$_3$)$_3$;
n. $R^6$=CH$_3$ and $R^{10b}$=CH$_2$NHC(O)-cyclopropyl;
o. $R^6$=CH$_3$ and $R^{10b}$=CH$_2$NHC(O)CH$_2$N(CH$_3$)$_2$;
p. $R^6$=CD$_3$ and $R^{10b}$=NH$_2$;
q. $R^6$=CD$_3$ and $R^{10b}$=NHC(O)CH$_2$OCH$_3$;
r. $R^6$=CD$_3$ and $R^{10b}$=NHC(O)CH$_3$;
s. $R^6$=CD$_3$ and $R^{10b}$=NHC(O)-cyclopropyl;
t. $R^6$=CD$_3$ and $R^{10b}$=NHC(O)(CH$_2$)$_5$CH$_3$;
u. $R^6$=CD$_3$ and $R^{10b}$=NHC(O)CH$_2$OCH$_2$CH$_3$;
v. $R^6$=CD$_3$ and $R^{10b}$=NHC(O)CH$_2$N(CH$_3$)$_2$;
w. $R^6$=CD$_3$ and $R^{10b}$=NHC(O)CH$_2$Cl;
x. $R^6$=CD$_3$ and $R^{10b}$=NHC(O)OCH$_2$CH$_3$;
y. $R^6$=CD$_3$ and $R^{10b}$=CH$_2$NHC(O)OC(CH$_3$)$_3$;
z. $R^6$=CD$_3$ and $R^{10b}$=CH$_2$NHC(O)CH$_3$;
aa. $R^6$=CD$_3$ and $R^{10b}$=CH$_2$NHC(O)(CH$_2$)$_5$CH$_3$;
bb. $R^6$=CD$_3$ and $R^{10b}$=CH$_2$NHC(O)CH$_2$C(CH$_3$)$_3$;
cc. $R^6$=CD$_3$ and $R^{10b}$=CH$_2$NHC(O)-cyclopropyl;
dd. $R^6$=CD$_3$ and $R^{10b}$=CH$_2$NHC(O)CH$_2$N(CH$_3$)$_2$;
ee. $R^6$=CH$_3$ and $R^{10b}$=NHC(O)CD$_2$OCD$_3$;
ff. $R^6$=CH$_3$ and $R^{10b}$=NHC(O)CD$_3$;
gg. $R^6$=CH$_3$ and $R^{10b}$=NHC(O)-d$_5$-cyclopropyl;
hh. $R^6$=CH$_3$ and $R^{10b}$=NHC(O)(CD$_2$)$_5$CD$_3$;
ii. $R^6$=CH$_3$ and $R^{10b}$=NHC(O)CD$_2$OCD$_2$CD$_3$;
jj. $R^6$=CH$_3$ and $R^{10b}$=NHC(O)CD$_2$N(CD$_3$)$_2$;
kk. $R^6$=CH$_3$ and $R^{10b}$=NHC(O)CD$_2$Cl;
ll. $R^6$=CH$_3$ and $R^{10b}$=NHC(O)OCD$_2$CD$_3$;
mm. $R^6$=CH$_3$ and $R^{10b}$=CD$_2$NHC(O)OC(CD$_3$)$_3$;
nn. $R^6$=CH$_3$ and $R^{10b}$=CD$_2$NHC(O)CD$_3$;

oo. $R^6$=CH$_3$ and $R^{10b}$=CD$_2$NHC(O)(CD$_2$)$_5$CD$_3$;
pp. $R^6$=CH$_3$ and $R^{10b}$=CD$_2$NHC(O)CD$_2$C(CD$_3$)$_3$;
qq. $R^6$=CH$_3$ and $R^{10b}$=CD$_2$NHC(O)-d$_5$-cyclopropyl;
rr. $R^6$=CH$_3$ and $R^{10b}$=CD$_2$NHC(O)CD$_2$N(CD$_3$)$_2$;
ss. $R^6$=CD$_3$ and $R^{10b}$=NHC(O)CD$_2$OCD$_3$;
tt. $R^6$=CD$_3$ and $R^{10b}$=NHC(O)CD$_3$;
uu. $R^6$=CD$_3$ and $R^{10b}$=NHC(O)-d$_5$-cyclopropyl;
vv. $R^6$=CD$_3$ and $R^{10b}$=NHC(O)(CD$_2$)$_5$CD$_3$;
ww. $R^6$=CD$_3$ and $R^{10b}$=NHC(O)CD$_2$OCD$_2$CD$_3$;
xx. $R^6$=CD$_3$ and $R^{10b}$=NHC(O)CD$_2$N(CD$_3$)$_2$;
yy. $R^6$=CD$_3$ and $R^{10b}$=NHC(O)CD$_2$Cl;
zz. $R^6$=CD$_3$ and $R^{10b}$=NHC(O)OCD$_2$CD$_3$;
aaa. $R^6$=CD$_3$ and $R^{10b}$=CD$_2$NHC(O)OC(CD$_3$)$_3$;
bbb. $R^6$=CD$_3$ and $R^{10b}$=CD$_2$NHC(O)CD$_3$;
ccc. $R^6$=CD$_3$ and $R^{10b}$=CD$_2$NHC(O)(CD$_2$)$_5$CD$_3$;
ddd. $R^6$=CD$_3$ and $R^{10b}$=CD$_2$NHC(O)CD$_2$C(CD$_3$)$_3$;
eee. $R^6$=CD$_3$ and $R^{10b}$=CD$_2$NHC(O)-d$_5$-cyclopropyl; and,
fff. $R^6$=CD$_3$ and $R^{10b}$=CD$_2$NHC(O)CD$_2$N(CD$_3$)$_2$;

and pharmaceutically acceptable salts and solvates thereof, wherein:

Z is H or D, provided that the abundance of deuterium in Z is at least 30%;

$R^1$, $R^2$, $R^3$, $R^4$, $R^5$, $R^7$, $R^8$, and $R^9$ are independently selected from H and D; and wherein the compound of formulae IIIa or b has an enantiomeric excess, with respect to the C—Z carbon, of at least 5%.

In another aspect, the present invention provides deuterium-enriched compounds selected from:

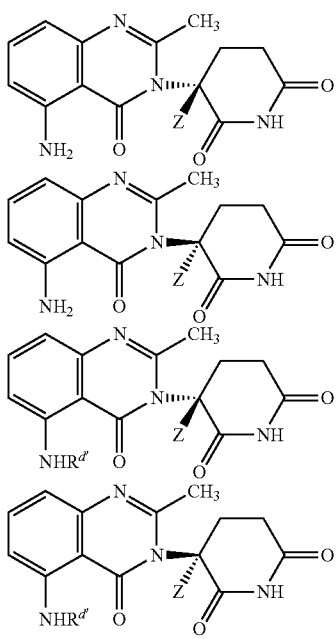

wherein:
a. $R^{d'}$=C(O)CH$_2$OCH$_3$;
b. $R^{d'}$=C(O)CH$_3$;
c. $R^{d'}$=C(O)-cyclopropyl;
d. $R^{d'}$=C(O)(CH$_2$)$_5$CH$_3$;
e. $R^{d'}$=C(O)CH$_2$OCH$_2$CH$_3$;
f. $R^{d'}$=C(O)CH$_2$N(CH$_3$)$_2$;
g. $R^{d'}$=C(O)CH$_2$Cl;
h. $R^{d'}$=C(O)OCH$_2$CH$_3$;
i. $R^{d'}$=NHC(O)CH$_2$CH$_2$CH$_3$;

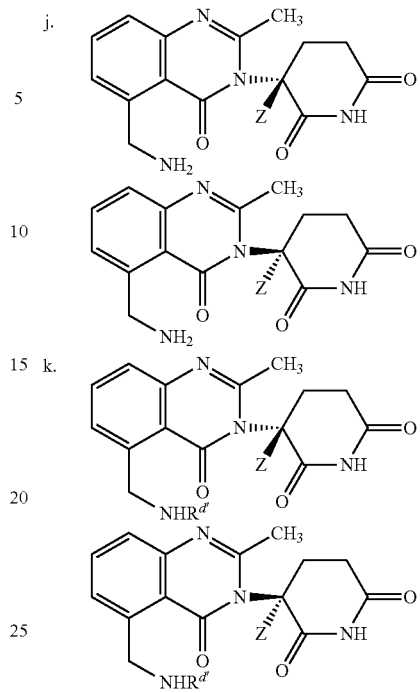

wherein:
l. $R^{d'}$=C(O)OC(CH$_3$)$_3$;
m. $R^{d'}$=C(O)CH$_3$;
n. $R^{d'}$=C(O)(CH$_2$)$_5$CH$_3$;
o. $R^{d'}$=C(O)CH$_2$C(CH$_3$)$_3$;
p. $R^{d'}$=C(O)-cyclopropyl; or
q. $R^{d'}$=C(O)CH$_2$N(CH$_3$)$_2$;

and pharmaceutically acceptable salts and solvates thereof, wherein the compound has an enantiomeric excess, with respect to the C—Z carbon, of at least 5%.

In another aspect, the present invention provides deuterium-enriched compounds of formulae Ia-If, wherein $R^{10}$=$R^{10c}$ (compounds IVa-IVf)), and pharmaceutically acceptable salts and solvates thereof In another aspect, $R^g$ is —(CH$_2$)$_n$-(6 to 10 membered aryl).

In another aspect, $R^g$ is —C(O)(CH$_2$)$_n$-(6 to 10 membered aryl) or —C(O)(CH$_2$)$_n$-(6 to 10 membered heteroaryl), wherein the aryl or heteroaryl is optionally substituted as described above.

In another aspect, $R^g$ is —C(O)(CH$_2$)$_n$—NHR$^h$, wherein R$^h$ is 6 to 10 membered aryl optionally substituted as described above.

In another aspect, $R^g$ is —C(O)(CH$_2$)$_n$O(CH$_2$)$_n$-(6 to 10 membered aryl).

In another aspect, $R^g$ is —C(O)-phenyl or —C(O)—CH$_2$-phenyl, wherein the phenyl is optionally substituted with a group selected from: methyl, CF$_3$, and halo.

In another aspect, $R^g$ is —C(O)NH-phenyl, wherein the phenyl is optionally substituted with a group selected from methyl, CF$_3$, and halo.

$R^6$ is hydrogen.

In another aspect, $R^{10}$=$R^{10c}$ and $R^6$ is —(CH$_2$)$_n$OH or hydroxyl.

In another aspect, $R^{10}$=$R^{10c}$ and $R^6$ is phenyl.

In another aspect, $R^{10}$=$R^{10c}$ and $R^6$ is —O(C$_1$-C$_6$)alkyl optionally substituted with one or more halo.

In another aspect, $R^{10}=R^{10c}$ and $R^6$ is $(C_1-C_6)$alkyl optionally substituted with one or more halo.

In another aspect, $R^{10}=R^{10c}$ and $R^6$ is methyl.

In another aspect, the present invention provides deuterium-enriched compounds of formulae IVa or IVb:

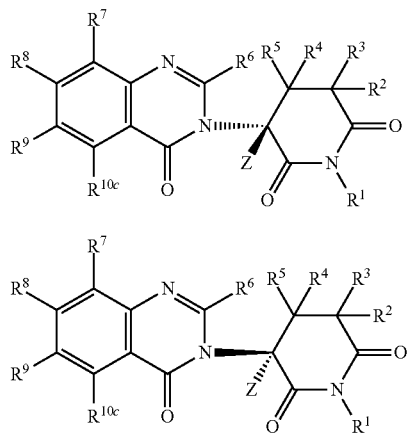

IVa

IVb wherein the compound is selected from:
a. $R^6=CH_3$ and $R^{10c}$=3-Cl-phenyl-C(O)NH—;
b. $R^6=CH_3$ and $R^{10c}$=phenyl-CH$_2$OCH$_2$C(O)NH—;
c. $R^6=CH_3$ and $R^{10c}$=phenyl-CH$_2$C(O)NHCH$_2$—;
d. $R^6=CH_3$ and $R^{10c}$=pyrid-2-ylC(O)NHCH$_2$—;
e. $R^6=CH_3$ and $R^{10c}$=4-Cl-phenyl-CH$_2$C(O)NHCH$_2$—;
f. $R^6=CH_3$ and $R^{10c}$=4-CF$_3$O-phenyl-CH$_2$C(O)NHCH$_2$—;
g. $R^6=CH_3$ and $R^{10c}$=3,4-diCl-phenyl-CH$_2$C(O)NHCH$_2$—;
h. $R^6=CH_3$ and $R^{10c}$=4-F-phenyl-CH$_2$C(O)NHCH$_2$—;
i. $R^6=CH_3$ and $R^{10c}$=4-CH$_3$-3-F-phenyl-CH$_2$C(O)NHCH$_2$—;
j. $R^6=CH_3$ and $R^{10c}$=4-CF$_3$-phenyl-CH$_2$C(O)NHCH$_2$—;
k. $R^6=CH_3$ and $R^{10c}$=4-Cl-phenyl-NHC(O)NHCH$_2$—;
l. $R^6=CH_3$ and $R^{10c}$=4-CH$_3$-3-Cl-phenyl-NHC(O)NHCH$_2$—;
m. $R^6=CH_3$ and $R^{10c}$=3,4-diCH$_3$-phenyl-NHC(O)NHCH$_2$—;
n. $R^6=CH_3$ and $R^{10c}$=4-CH$_3$-phenyl-NHC(O)NHCH$_2$—;
o. $R^6=CH_3$ and $R^{10c}$=3-CH$_3$-phenyl-NHC(O)NHCH$_2$—;
p. $R^6=CH_3$ and $R^{10c}$=4-Cl-phenylC(O)NHCH$_2$—;
q. $R^6=CH_3$ and $R^{10c}$=3-F-phenylC(O)NHCH$_2$—;
r. $R^6=CH_3$ and $R^{10c}$=4-CF$_3$-phenylC(O)NHCH$_2$—;
s. $R^6=CH_3$ and $R^{10c}$=4-CF$_3$O-phenylC(O)NHCH$_2$—;
t. $R^6=CH_3$ and $R^{10c}$=phenylC(O)NHCH$_2$—;
u. $R^6=CH_3$ and $R^{10c}$=3,4-diCl-phenylC(O)NHCH$_2$—;
v. $R^6=CH_3$ and $R^{10c}$=3-CF$_3$-phenylC(O)NHCH$_2$—;
w. $R^6=CH_3$ and $R^{10c}$=4-CF$_3$S-phenylC(O)NHCH$_2$—;
x. $R^6=CH_3$ and $R^{10c}$=4-CH$_3$-3-Cl-phenylC(O)NHCH$_2$—;
y. $R^6=CD_3$ and $R^{10c}$=3-Cl-phenyl-C(O)NH—;
z. $R^6=CD_3$ and $R^{10c}$=phenyl-CH$_2$OCH$_2$C(O)NH—;
aa. $R^6=CD_3$ and $R^{10c}$=phenyl-CH$_2$C(O)NHCH$_2$—;
bb. $R^6=CD_3$ and $R^{10c}$=pyrid-2-ylC(O)NHCH$_2$—;
cc. $R^6=CD_3$ and $R^{10c}$=4-Cl-phenyl-CH$_2$C(O)NHCH$_2$—;
dd. $R^6=CD_3$ and $R^{10c}$=4-CF$_3$O-phenyl-CH$_2$C(O)NHCH$_2$—;
ee. $R^6=CD_3$ and $R^{10c}$=3,4-diCl-phenyl-CH$_2$C(O)NHCH$_2$—;
ff. $R^6=CD_3$ and $R^{10c}$=4-F-phenyl-CH$_2$C(O)NHCH$_2$—;
gg. $R^6=CD_3$ and $R^{10c}$=4-CH$_3$-3-F-phenyl-CH$_2$C(O)NHCH$_2$—;
hh. $R^6=CD_3$ and $R^{10c}$=4-CF$_3$-phenyl-CH$_2$C(O)NHCH$_2$—;
ii. $R^6=CD_3$ and $R^{10c}$=4-Cl-phenyl-NHC(O)NHCH$_2$—;
jj. $R^6=CD_3$ and $R^{10c}$=4-CH$_3$-3-Cl-phenyl-NHC(O)NHCH$_2$—;
kk. $R^6=CD_3$ and $R^{10c}$=3,4-diCH$_3$-phenyl-NHC(O)NHCH$_2$—;
ll. $R^6=CD_3$ and $R^{10c}$=4-CH$_3$-phenyl-NHC(O)NHCH$_2$—;
mm. $R^6=CD_3$ and $R^{10c}$=3-CH$_3$-phenyl-NHC(O)NHCH$_2$—;
nn. $R^6=CD_3$ and $R^{10c}$=4-Cl-phenylC(O)NHCH$_2$—;
oo. $R^6=CD_3$ and $R^{10c}$=3-F-phenylC(O)NHCH$_2$—;
pp. $R^6=CD_3$ and $R^{10c}$=4-CF$_3$-phenylC(O)NHCH$_2$—;
qq. $R^6=CD_3$ and $R^{10c}$=4-CF$_3$O-phenylC(O)NHCH$_2$—;
rr. $R^6=CD_3$ and $R^{10c}$=phenylC(O)NHCH$_2$—;
ss. $R^6=CD_3$ and $R^{10c}$=3,4-diCl-phenylC(O)NHCH$_2$—;
tt. $R^6=CD_3$ and $R^{10c}$=3-CF$_3$-phenylC(O)NHCH$_2$—;
uu. $R^6=CD_3$ and $R^{10c}$=4-CF$_3$S-phenylC(O)NHCH$_2$—;
vv. $R^6=CD_3$ and $R^{10c}$=4-CH$_3$-3-Cl-phenylC(O)NHCH$_2$—;
ww. $R^6=CH_3$ and $R^{16c}$=phenyl-CD$_2$OCD$_2$C(O)NH—;
xx. $R^6=CH_3$ and $R^{16c}$=phenyl-CD$_2$C(O)NHCD$_2$-;
yy. $R^6=CH_3$ and $R^{10c}$=pyrid-2-ylC(O)NHCD$_2$-;
zz. $R^6=CH_3$ and $R^{16c}$=4-Cl-phenyl-CD$_2$C(O)NHCD$_2$-;
aaa. $R^6=CH_3$ and $R^{16c}$=4-CF$_3$O-phenyl-CD$_2$C(O)NHCD$_2$-;
bbb. $R^6=CH_3$ and $R^{10c}$=3,4-diCl-phenyl-CD$_2$C(O)NHCD$_2$-;
ccc. $R^6=CH_3$ and $R^{16c}$=4-F-phenyl-CD$_2$C(O)NHCD$_2$-;
ddd. $R^6=CH_3$ and $R^{10c}$=4-CD$_3$-3-F-phenyl-CD$_2$C(O)NHCD$_2$-;
eee. $R^6=CH_3$ and $R^{16c}$=4-CF$_3$-phenyl-CD$_2$C(O)NHCD$_2$-;
fff. $R^6=CH_3$ and $R^{10c}$=4-Cl-phenyl-NHC(O)NHCD$_2$-;
ggg. $R^6=CH_3$ and $R^{10c}$=4-CD$_3$-3-Cl-phenyl-NHC(O)NHCD$_2$-;
hhh. $R^6=CH_3$ and $R^{10c}$=3,4-diCD$_3$-phenyl-NHC(O)NHCD$_2$-;
iii. $R^6=CH_3$ and $R^{10c}$=4-CD$_3$-phenyl-NHC(O)NHCD$_2$-;
jjj. $R^6=CH_3$ and $R^{10c}$=3-CD$_3$-phenyl-NHC(O)NHCD$_2$-;
kkk. $R^6=CH_3$ and $R^{10c}$=4-Cl-phenylC(O)NHCD$_2$-;
lll. $R^6=CH_3$ and $R^{10c}$=3-F-phenylC(O)NHCD$_2$-;
mmm. $R^6=CH_3$ and $R^{10c}$=4-CF$_3$-phenylC(O)NHCD$_2$-;
nnn. $R^6=CH_3$ and $R^{10c}$=4-CF$_3$O-phenylC(O)NHCD$_2$-;
ooo. $R^6=CH_3$ and $R^{16c}$=phenylC(O)NHCD$_2$-;
ppp. $R^6=CH_3$ and $R^{10c}$=3,4-diCl-phenylC(O)NHCD$_2$-;
qqq. $R^6=CH_3$ and $R^{10c}$=3-CF$_3$-phenylC(O)NHCD$_2$-;
rrr. $R^6=CH_3$ and $R^{10c}$=4-CF$_3$S-phenylC(O)NHCD$_2$-;
sss. $R^6=CH_3$ and $R^{10c}$=4-CD$_3$-3-Cl-phenylC(O)NHCD$_2$-;
ttt. $R^6=CD_3$ and $R^{10c}$=phenyl-CD$_2$OCD$_2$C(O)NH—;
uuu. $R^6=CD_3$ and $R^{10c}$=phenyl-CD$_2$C(O)NHCD$_2$-;
vvv. $R^6=CD_3$ and $R^{10c}$=pyrid-2-ylC(O)NHCD$_2$-;
www. $R^6=CD_3$ and $R^{10c}$=4-Cl-phenyl-CD$_2$C(O)NHCD$_2$-;
xxx. $R^6=CD_3$ and $R^{10c}$=4-CF$_3$O-phenyl-CD$_2$C(O)NHCD$_2$-;
yyy. $R^6=CD_3$ and $R^{10c}$=3,4-diCl-phenyl-CD$_2$C(O)NHCD$_2$-;
zzz. $R^6=CD_3$ and $R^{10c}$=4-F-phenyl-CD$_2$C(O)NHCD$_2$-;
aaaa. $R^6=CD_3$ and $R^{10c}$=4-CD$_3$-3-F-phenyl-CD$_2$C(O)NHCD$_2$-;
bbbb. $R^6=CD_3$ and $R^{10c}$=4-CF$_3$-phenyl-CD$_2$C(O)NHCD$_2$-;
cccc. $R^6=CD_3$ and $R^{10c}$=4-Cl-phenyl-NHC(O)NHCD$_2$-;
dddd. $R^6=CD_3$ and $R^{10c}$=4-CD$_3$-3-Cl-phenyl-NHC(O)NHCD$_2$-;
eeee. $R^6=CD_3$ and $R^{10c}$=3,4-diCD$_3$-phenyl-NHC(O)NHCD$_2$-;
ffff. $R^6=CD_3$ and $R^{10c}$=4-CD$_3$-phenyl-NHC(O)NHCD$_2$-;
gggg. $R^6=CD_3$ and $R^{10c}$=3-CD$_3$-phenyl-NHC(O)NHCD$_2$-;
hhhh. $R^6=CD_3$ and $R^{10c}$=4-Cl-phenylC(O)NHCD$_2$-;
iiii. $R^6=CD_3$ and $R^{10c}$=3-F-phenylC(O)NHCD$_2$-;
jjjj. $R^6=CD_3$ and $R^{10c}$=4-CF$_3$-phenylC(O)NHCD$_2$-;
kkkk. $R^6=CD_3$ and $R^{10c}$=4-CF$_3$O-phenylC(O)NHCD$_2$-;
llll. $R^6=CD_3$ and $R^{10c}$=phenylC(O)NHCD$_2$-;
mmmm. $R^6=CD_3$ and $R^{10c}$=3,4-diCl-phenylC(O)NHCD$_2$-;
nnnn. $R^6=CD_3$ and $R^{10c}$=3-CF$_3$-phenylC(O)NHCD$_2$-;
oooo. $R^6=CD_3$ and $R^{10c}$=4-CF$_3$S-phenylC(O)NHCD$_2$-; and,
pppp. $R^6=CD_3$ and $R^{10c}$=4-CD$_3$-3-Cl-phenylC(O)NHCD$_2$-;

and pharmaceutically acceptable salts and solvates thereof, wherein:

Z is H or D, provided that the abundance of deuterium in Z is at least 30%;

$R^1$, $R^2$, $R^3$, $R^4$, $R^5$, $R^7$, $R^8$, and $R^9$ are independently selected from H and D; and wherein the compound of formulae IVa or IVb has an enantiomeric excess, with respect to the C—Z carbon, of at least 5%.

In another aspect, the present invention provides deuterium-enriched compounds selected from:

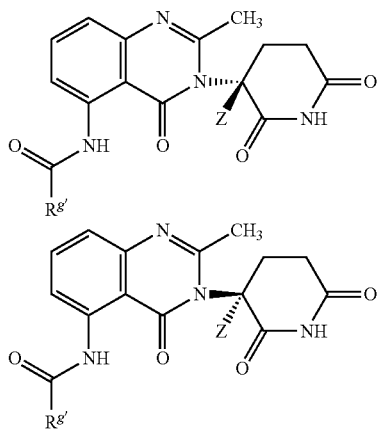

wherein:
a. $R^{g'}$=3-Cl-phenyl;
b. $R^{g'}$=phenyl-$CH_2OCH_2$—;

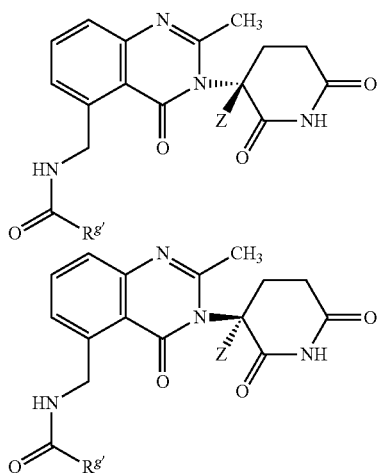

wherein:
c. $R^{g'}$=phenyl-$CH_2$—;
d. $R^{g'}$=pyrid-2-yl-;
e. $R^{g'}$=4-Cl-phenyl-$CH_2$-;
f. $R^{g'}$=4-$CF_3$O-phenyl-$CH_2$—;
g. $R^{g'}$=3,4-diCl-phenyl-$CH_2$—;
h. $R^{g'}$=4-F-phenyl-$CH_2$—;
i. $R^{g'}$=4-$CH_3$-3-F-phenyl-$CH_2$—;
j. $R^{g'}$=4-$CF_3$-phenyl-$CH_2$—;
k. $R^{g'}$=4-Cl-phenyl-NH—;
l. $R^{g'}$=4-$CH_3$-3-Cl-phenyl-NH—;
m. $R^{g'}$=3,4-di$CH_3$-phenyl-NH—;
n. $R^{g'}$=4-$CH_3$-phenyl-NH—;
o. $R^{g'}$=3-$CH_3$-phenyl-NH—;
p. $R^{g'}$=4-Cl-phenyl-;
q. $R^{g'}$=3-F-phenyl-;
r. $R^{g'}$=4-$CF_3$-phenyl-;
s. $R^{g'}$=4-$CF_3$O-phenyl-;
t. $R^{g'}$=phenyl-;
u. $R^{g'}$=3,4-diCl-phenyl-;
v. $R^{g'}$=3-$CF_3$-phenyl-;
w. $R^{g'}$=4-$CF_3$S-phenyl-; and
x. $R^{g'}$=4-$CH_3$-3-Cl-phenyl-;

and pharmaceutically acceptable salts and solvates thereof, wherein the compound has an enantiomeric excess, with respect to the C—Z carbon, of at least 5%.

In another aspect, the present invention provides deuterium-enriched compounds selected from:

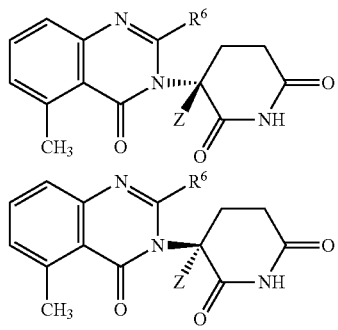

wherein:
a. $R^6$=H;
b. $R^6$=OH;
c. $R^6$=$CH_2CH_3$ where one or more H in $R^6$ are optionally replaced with D;
d. $R^6$=$CH_2CH_2CH_3$ where one or more H in $R^6$ are optionally replaced with D;
e. $R^6$=$CF_3$;
f. $R^6$=phenyl where one or more H in $R^6$ are optionally replaced with D;
g. $R^6$=$CH_3$ where one or more H in $R^6$ are optionally replaced with D;

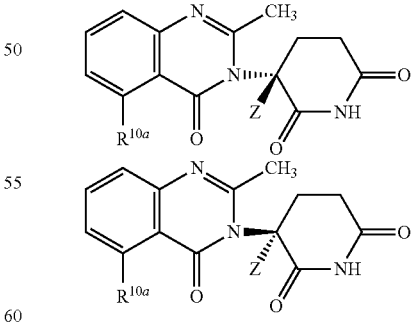

wherein:
h. $R_{10a}$=$OCH_3$ where one or more H in $R^{10a}$ are optionally replaced with D;
i. $R^{10a}$=F;
j. $R^{10a}$=Cl;
k. $R^{10a}$=$CF_3$; and, l.

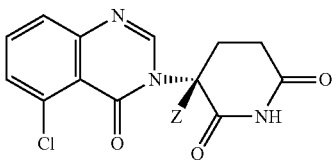

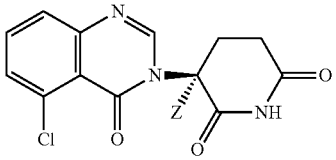

and pharmaceutically acceptable salts and solvates thereof, wherein the compound has an enantiomeric excess, with respect to the C—Z carbon, of at least 5%.

In another aspect, the present invention provides a deuterium-enriched compound selected from:

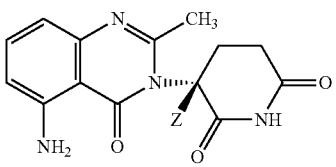

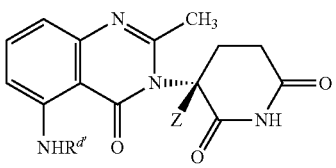

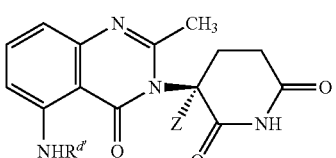

wherein:
a. $R^{d'}$=C(O)CH$_2$OCH$_3$;
b. $R^{d'}$=C(O)CH$_3$;
c. $R^{d'}$=C(O)-cyclopropyl;
d. $R^{d'}$=C(O)(CH$_2$)$_5$CH$_3$;
e. $R^{d'}$=C(O)CH$_2$OCH$_2$CH$_3$;
f. $R^{d'}$=C(O)CH$_2$N(CH$_3$)$_2$;
g. $R^{d'}$=C(O)CH$_2$Cl;
h. $R^{d'}$=C(O)OCH$_2$CH$_3$;
i. $R^{d'}$=NHC(O)CH$_2$CH$_2$CH$_3$; wherein for each of the foregoing $R^{d'}$ one or more H is optionally replaced with D;

j.

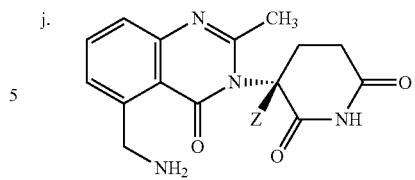

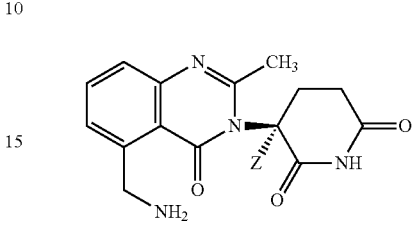

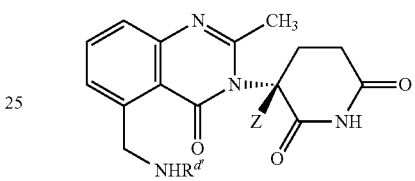

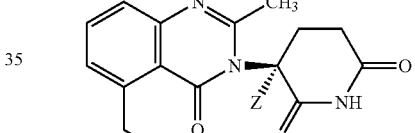

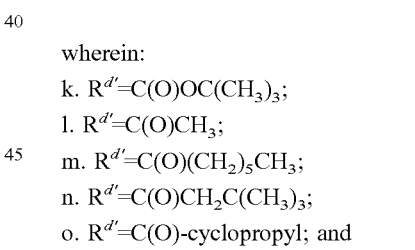

wherein:
k. $R^{d'}$=C(O)OC(CH$_3$)$_3$;
l. $R^{d'}$=C(O)CH$_3$;
m. $R^{d'}$=C(O)(CH$_2$)$_5$CH$_3$;
n. $R^{d'}$=C(O)CH$_2$C(CH$_3$)$_3$;
o. $R^{d'}$=C(O)-cyclopropyl; and
p. $R^{d'}$=C(O)CH$_2$N(CH$_3$)$_2$;

and pharmaceutically acceptable salts and solvates thereof, wherein the compound has an enantiomeric excess, with respect to the C—Z carbon, of at least 5%.

In another aspect, the present invention provides a deuterium-enriched compound selected from:

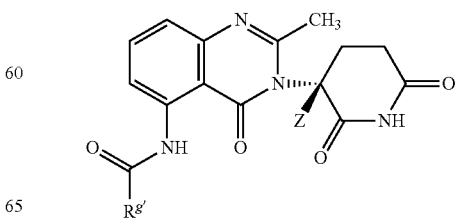

-continued

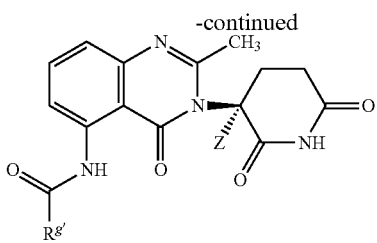

wherein:
   a. R^(g′)=3-Cl-phenyl;
   b. R^(g′)=phenyl-CH$_2$OCH$_2$—;

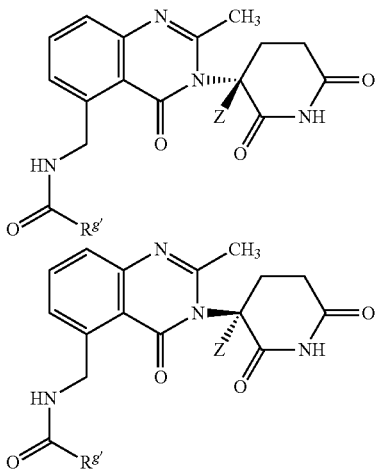

wherein:
   c. R^(g′)=phenyl-CH$_2$—;
   d. R^(g′)=pyrid-2-yl-;
   e. R^(g′)=4-Cl-phenyl-CH$_2$—;
   f. R^(g′)=4-CF$_3$O-phenyl-CH$_2$—;
   g. R^(g′)=3,4-diCl-phenyl-CH$_2$—;
   h. R^(g′)=4-F-phenyl-CH$_2$—;
   i. R^(g′)=4-CH$_3$-3-F-phenyl-CH$_2$—;
   j. R^(g′)=4-CF$_3$-phenyl-CH$_2$—;
   k. R^(g′)=4-Cl-phenyl-NH—;
   l. R^(g′)=4-CH$_3$-3-Cl-phenyl-NH—;
   m. R^(g′)=3,4-diCH$_3$-phenyl-NH—;
   n. R^(g′)=4-CH$_3$-phenyl-NH—;
   o. R^(g′)=3-CH$_3$-phenyl-NH—;
   p. R^(g′)=4-Cl-phenyl-;
   q. R^(g′)=3-F-phenyl-;
   r. R^(g′)=4-CF$_3$-phenyl-;
   s. R^(g′)=4-CF$_3$O-phenyl-;
   t. R^(g′)=phenyl-;
   u. R^(g′)=3,4-diCl-phenyl-;
   v. R^(g′)=3-CF$_3$-phenyl-;
   w. R^(g′)=4-CF$_3$S-phenyl-; and
   x. R^(g′)=4-CH$_3$-3-Cl-phenyl-; wherein for each of the foregoing R^(g′) one or more H is optionally replaced with D; and pharmaceutically acceptable salts and solvates thereof, wherein the compound has an enantiomeric excess, with respect to the C—Z carbon, of at least 5%.

Additional exemplary compounds are provided in Tables 1-15 below where variable Z is H or D, provided that the abundance of deuterium in Z is at least 30%.

Table 1 provides compounds that are representative examples of the present invention wherein the compound is of Formula I and the non-specified groups are as defined above for Formula I and the compounds have an enantiomeric excess, with respect to the C—Z carbon, of at least 5%.

TABLE 1

| Compound No. | Variable Definition |
|---|---|
| 1 | $R^1$, $R^2$, $R^3$, $R^4$, $R^5$, $R^7$, $R^8$, and $R^9$ = H |
| 2 | $R^1$, $R^2$, $R^3$, $R^4$, $R^5$, $R^7$, $R^8$, and $R^9$ = D |
| 3 | $R^2$-$R^3$ = D |
| 4 | $R^4$-$R^5$ = D |
| 5 | $R^2$-$R^5$ = D |
| 6 | $R^7$-$R^9$ = D |

Table 2 provides compounds that are representative examples of the present invention wherein the compound is of Formula Ia and the non-specified groups are as defined above for Formula Ia and the compounds have an enantiomeric excess, with respect to the C—Z carbon, of at least 5%.

TABLE 2

| Compound No. | Variable Definition |
|---|---|
| 1 | $R^1$, $R^2$, $R^3$, $R^4$, $R^5$, $R^7$, $R^8$, and $R^9$ = H |
| 2 | $R^1$, $R^2$, $R^3$, $R^4$, $R^5$, $R^7$, $R^8$, and $R^9$ = D |
| 3 | $R^2$-$R^3$ = D |
| 4 | $R^4$-$R^5$ = D |
| 5 | $R^2$-$R^5$ = D |
| 6 | $R^7$-$R^9$ = D |

Table 3 provides compounds that are representative examples of the present invention wherein the compound is of Formula Ib and the non-specified groups are as defined above for Formula Ib and the compounds have an enantiomeric excess, with respect to the C—Z carbon, of at least 5%.

TABLE 3

| Compound No. | Variable Definition |
|---|---|
| 1 | $R^1$, $R^2$, $R^3$, $R^4$, $R^5$, $R^7$, $R^8$, and $R^9$ = H |
| 2 | $R^1$, $R^2$, $R^3$, $R^4$, $R^5$, $R^7$, $R^8$, and $R^9$ = D |
| 3 | $R^2$-$R^3$ = D |
| 4 | $R^4$-$R^5$ = D |
| 5 | $R^2$-$R^5$ = D |
| 6 | $R^7$-$R^9$ = D |

Table 4 provides compounds that are representative examples of the present invention wherein the compound is of Formula IIa and the non-specified groups are as defined above for Formula IIa and the compounds have an enantiomeric excess, with respect to the C—Z carbon, of at least 5%.

TABLE 4

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 5 provides compounds that are representative examples of the present invention wherein the compound is of Formula IIb and the non-specified groups are as defined above for Formula IIb and the compounds have an enantiomeric excess, with respect to the C—Z carbon, of at least 5%.

TABLE 5

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 6 provides compounds that are representative examples of the present invention wherein the compound is of Formula IIIa and the non-specified groups are as defined above for Formula IIIa and the compounds have an enantiomeric excess, with respect to the C—Z carbon, of at least 5%.

TABLE 6

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 7 provides compounds that are representative examples of the present invention wherein the compound is of Formula IIIb and the non-specified groups are as defined above for Formula IIIb and the compounds have an enantiomeric excess, with respect to the C—Z carbon, of at least 5%.

TABLE 7

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 8 provides compounds that are representative examples of the present invention wherein the compound is of Formula IVa and the non-specified groups are as defined above for Formula IVa and the compounds have an enantiomeric excess, with respect to the C—Z carbon, of at least 5%.

TABLE 8

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 9 provides compounds that are representative examples of the present invention wherein the compound is of Formula IVb and the non-specified groups are as defined above for Formula IVb and the compounds have an enantiomeric excess, with respect to the C—Z carbon, of at least 5%.

TABLE 9

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

Table 10 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 10

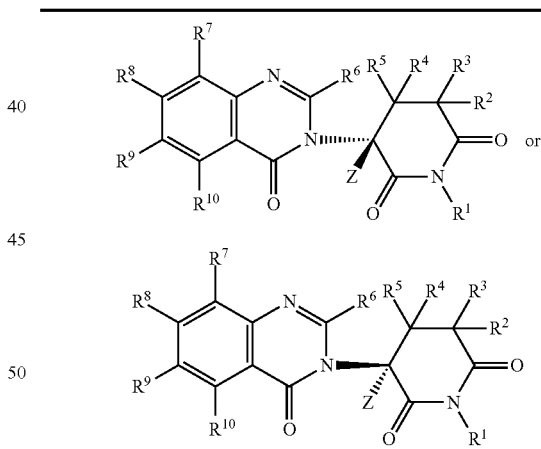

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2-R^3$ = D |
| 4 | $R^4-R^5$ = D |
| 5 | $R^2-R^5$ = D |
| 6 | $R^7-R^9$ = D |

$R^6 = CH_3$
$R^{10} = CH_3$

Table 11 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 11

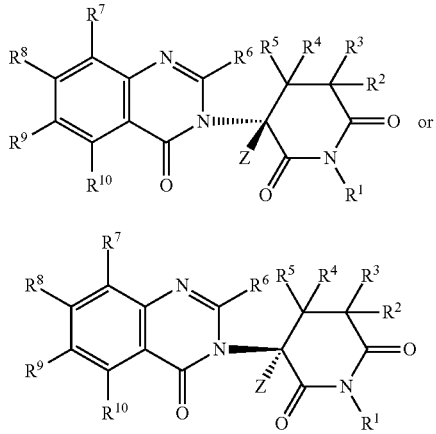

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2$-$R^3$ = D |
| 4 | $R^4$-$R^5$ = D |
| 5 | $R^2$-$R^5$ = D |
| 6 | $R^7$-$R^9$ = D |

$R^6 = CD_3$
$R^{10} = CH_3$

Table 12 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 12

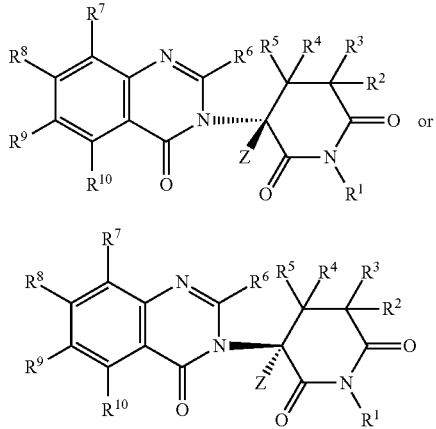

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2$-$R^3$ = D |
| 4 | $R^4$-$R^5$ = D |

TABLE 12-continued

| 5 | $R^2$-$R^5$ = D |
|---|---|
| 6 | $R^7$-$R^9$ = D |

$R^6 = CH_3$
$R^{10} = CD_3$

Table 13 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 13

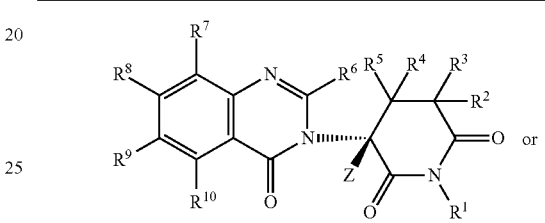

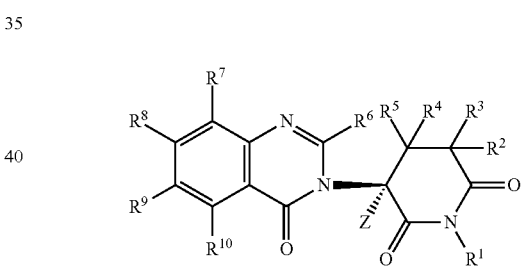

| Compound No. | Variable Definition |
|---|---|
| 1 | $R^1, R^2, R^3, R^4, R^5, R^7, R^8$, and $R^9$ = H |
| 2 | $R^1, R^2, R^3, R^4, R^5, R^7, R^8$, and $R^9$ = D |
| 3 | $R^2$-$R^3$ = D |
| 4 | $R^4$-$R^5$ = D |
| 5 | $R^2$-$R^5$ = D |
| 6 | $R^7$-$R^9$ = D |

$R^6 = CD_3$
$R^{10} = CD_3$

Table 14 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 14

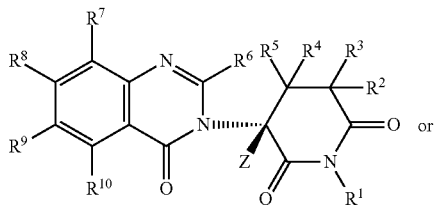

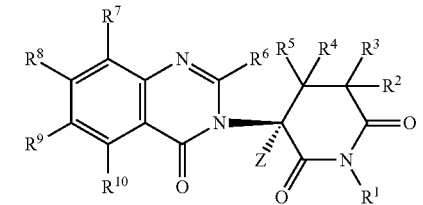

| Compound No. | Variable Definition |
|---|---|
| 1 | $R^1, R^2, R^3, R^4, R^5, R^7, R^8,$ and $R^9$ = H |
| 2 | $R^1, R^2, R^3, R^4, R^5, R^7, R^8,$ and $R^9$ = D |
| 3 | $R^2\text{-}R^3$ = D |
| 4 | $R^4\text{-}R^5$ = D |
| 5 | $R^2\text{-}R^5$ = D |
| 6 | $R^7\text{-}R^9$ = D |

$R^6$ = $CH_3$
$R^{10}$ = $NH_2$

Table 15 provides compounds that are representative examples of the present invention wherein the compounds are of the formulae below and the non-specified groups are as defined above for Formula I and the compounds have an enantiomeric excess, with respect to the C—Z carbon, of at least 5%.

TABLE 15

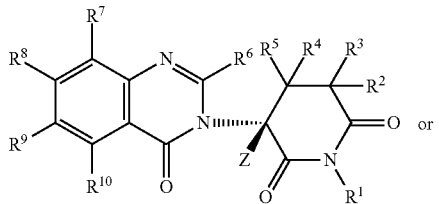

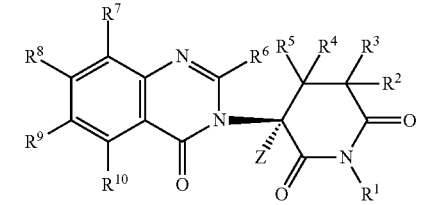

| Compound No. | Variable Definition |
|---|---|
| 1 | $R^1, R^2, R^3, R^4, R^5, R^7, R^8,$ and $R^9$ = H |
| 2 | $R^1, R^2, R^3, R^4, R^5, R^7, R^8,$ and $R^9$ = D |
| 3 | $R^2\text{-}R^3$ = D |
| 4 | $R^4\text{-}R^5$ = D |
| 5 | $R^2\text{-}R^5$ = D |
| 6 | $R^7\text{-}R^9$ = D |

$R^6$ = $CD_3$
$R^{10}$ = $NH_2$

Another aspect of the invention provides a compound recited above where a hydrogen atom present in any substituent is optionally replaced by D.

The present invention is based on stabilizing 3-(5-substituted-4-oxoquinazolin-3(4H)-yl)-3-deutero-piperidine-2,6-diones via deuteration at the 3-position. The C-D bond at the 3-position is stronger than the naturally occurring C—H bond. The 3-deuterium is expected to slow the racemization of the stereogenic center at the 3-position.

With hydrogen atoms being present in formulae I-IVf, the 3-(5-substituted-4-oxoquinazolin-3(4H)-yl)-3-deutero-piperidine-2,6-diones of the present invention can be enriched beyond the 3-position. For example, in formula I replacing one of $R^1\text{-}R^5$, $R^6\text{-}R^9$ with a deuterium would result in a ~11% enrichment (9 starting hydrogens, 1/9×100=~11%). Thus examples of additional enrichment of the 3-deutero-compounds of formula I include, but are not limited to, ~22% (2 additional deuteriums), ~33%, ~44%, ~55%, ~66%, ~77%, ~88%, and ~100% enrichment. In order to achieve additional enrichment less than about 11%, only partial deuteration of one site is required.

For other compounds of the present invention, enrichment beyond the 3-position includes the presence of at least one additional deuterium. For example, enrichment can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc., up to the total number of hydrogen atoms present and depending on the number of hydrogens present.

The invention also relates to isolated or purified 3-(5-substituted-4-oxoquinazolin-3(4H)-yl)-3-deutero-piperidine-2,6-diones. The isolated or purified 3-(5-substituted-4-oxoquinazolin-3(4H)-yl)-3-deutero-piperidine-2,6-diones is a group of molecules (i.e., an isolated compound) whose deuterium levels are above the naturally occurring levels. The isolated or purified 3-(5-substituted-4-oxoquinazolin-3(4H)-yl)-3-deutero-piperidine-2,6-diones can be obtained by techniques known to those of skill in the art.

Isolated means that the non-naturally occurring 3-(5-substituted-4-oxoquinazolin-3(4H)-yl)-3-deutero-piperidine-2,6-diones is purified (e.g., from the reaction solution in which it was prepared). Examples of the purity of the isolated 3-(5-substituted-4-oxoquinazolin-3(4H)-yl)-3-deutero-piperidine-2,6-diones (could be more than one type of compound) include, but are not limited to, at least 50%, 55%, 60%, 65%, 70%, 75%, 80%, 85%, 90%, 95%, to 100% with respect to non-deuterium-enriched 3-(5-substituted-4-oxoquinazolin-3(4H)-yl)-3-deutero-piperidine-2,6-dione components being present.

The invention also relates to mixture of compounds, which means that more than one type of deuterated compound is being claimed.

In another aspect, the present invention provides compositions comprising compounds of the present invention. The compositions require the presence of a compound of the present invention that is greater than its natural abundance. For example, the compositions of the present invention can comprise (a) a μg of a compound of the present invention; (b) from 1-10 μg; (c) a mg; (d) from 1-10 mg; (e) a gram; (f) from 1-10 grams; (g) from 1-100 grams; and, (h) a kg.

In another aspect, the invention provides an amount of a novel compound of the present invention. Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

In another aspect, the invention provides novel pharmaceutical compositions, comprising: a pharmaceutically acceptable carrier and a therapeutically effective amount of a deuterium-enriched compound of the invention.

In another aspect, the invention provides novel pharmaceutical compositions, comprising: a pharmaceutically acceptable carrier and a deuterium-enriched compound of the invention.

II. THERAPEUTIC APPLICATIONS

The invention provides methods of using deuterium-enriched compounds described herein to treat medical disorders. The deuterium-enriched compound can be, for example, a compound of Formula I, Formula I-A, or one of the other deuterium-enriched compounds described in Section I above. Various aspects of the invention pertaining to treating medical disorders is described below.

One aspect of the invention provides methods of treating, preventing, and/or managing various diseases or disorders using a compound provided herein, or a pharmaceutically acceptable salt, solvate (e.g., hydrate), or stereoisomer thereof. Without being limited by a particular theory, compounds provided herein are expected to control angiogenesis or inhibit the production of certain cytokines including, but not limited to, TNF-$\alpha$, IL-1$\beta$, IL-12, IL-18, GM-CSF, and/or IL-6. Without being limited by a particular theory, compounds provided herein may stimulate the production of certain other cytokines including IL-10, and also act as a costimulatory signal for T cell activation, resulting in increased production of cytokines such as, but are limited to, IFN-$\gamma$. In addition, compounds provided herein may enhance the effects of natural killer (NK) cells and antibody-mediated cellular cytotoxicity (ADCC). Further, compounds provided herein may be immunomodulatory and/or cytotoxic, and thus, may be useful as chemotherapeutic agents. Consequently, without being limited by a particular theory, some or all of such characteristics possessed by the compounds provided herein may render them useful in treating, managing, and/or preventing various diseases or disorders.

In another aspect, the invention provides for the use of an amount of a deuterium-enriched compound of the invention for the manufacture of a medicament (e.g., for treating, preventing, and/or managing angiogenesis and/or a cytokine related disorder). Yet another aspect of the invention provides a deuterium-enriched compound of the invention as described above for use in therapy.

Exemplary diseases or disorders include, but are not limited to, cancer, disorders associated with angiogenesis, pain including, but are not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNF-$\alpha$ related disorders, and other various diseases and disorders.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytoma, multiple brain metastases, glioblastoma multiforme, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karyotype acute myeloblastic leukemia, chronic lymphocytic leukemia (CLL), Hodgkin's lymphoma, non-Hodgkin's lymphoma, cutaneous T-cell lymphoma, cutaneous B-cell lymphoma, diffuse large B-cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressiva, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen-dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another aspect, the cancer is refractory or resistant to chemotherapy or radiation.

Accordingly, in certain embodiments, the cancer is an advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karyotype acute myeloblasts leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresceetable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma. In certain other embodiments, the cancer is a cancer of the bladder, bone, blood, brain, breast, cervix, chest, colon, endrometrium, esophagus, eye, head, kidney, liver, lymph node, lung, mouth, neck, ovary, pancreas, prostate, rectum, stomach, testis, throat, or uterus.

In certain embodiments, the cancer is a solid tumor or a blood born tumor. The solid tumor and/or blood borne tumor may be metastatic and/or drug resistant. In certain embodiments, the cancer is myeloma or lymphoma. In certain embodiments, the solid tumor is a hepatocellular carcinoma, glioblastoma, prostate cancer, colorectal cancer, ovarian cancer, or renal cancer.

In certain embodiments, the cancer is a non-Hodgkin's lymphoma that is a diffuse large B-cell lymphoma (such as characterized as being an activated B-cell phenotype). In yet other embodiments, the cancer is a non-Hodgkin's lymphoma that is a diffuse large B-cell lymphoma characterized by the expression of one or more biomarkers overexpressed in RIVA, U2932, TMD8, or OCI-Lyl O cell lines.

In certain embodiments, the cancer is relapsed or refractory.

In another aspect, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another aspect, provided herein are methods of treating, preventing or managing various types of lymphomas, including Non-Hodgkin's lymphoma (NHL). The term "lymphoma" refers to a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mantle zone lymphoma).

Additional exemplary diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis iridis (neovascularization of the angle of the eye). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

In certain embodiments, the disorder to be treated is an immune disease or an inflammatory disease. In certain other embodiments, the disorder to be treated is systemic lupus erythematosus, scleroderma, Sjogren syndrome, ANCA-induced vasculitis, anti-phospholipid syndrome, or myasthenia gravis. The scleroderma may be localized, systemic, limited, or diffuse scleroderma. In certain embodiments, the systemic scleroderma comprises CREST syndrome (Calcinosis, Raynaud's syndrome, esophagaeal dysfunction or dysmotility, sclerodactyly, telangiectasia). *Scleroderma* is also known as systemic sclerosis or progressive systemic sclerosis. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life. In certain embodiments, limited scleroderma is limited to the hands, the face, neck, or combinations thereof. In certain embodiments, diffuse scleroderma comprises skin tightening and also occurs above the wrists (or elbows). In yet other embodiments, diffuse systemic sclerosis is sine scleroderma, comprising internal organ fibrosis, but no skin tightening; or familial progressive systemic sclerosis.

In certain embodiments, the disorder to be treated is Raynaud's disease or syndrome.

Another aspect of the invention provides a method for reducing, inhibiting or preventing a symptom of systemic lupus erythematosus by administering to a patient suffering from systemic lupus erythematosus a deuterium-enriched compound described herein, wherein the symptom is one or more of joint pain, joint swelling, arthritis, chest pain when taking a deep breath, fatigue, fever with no other cause, general discomfort, uneasiness, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood, difficulty breathing, patchy skin color, or Raynaud's phenomenon.

Another aspect of the invention provides a method for reducing, inhibiting or preventing a symptom of scleroderma by administering to a patient suffering from scleroderma a deuterium-enriched compound described herein, wherein the symptom is one or more of (i) gradual hardening, thickening, and tightening of the skin; (ii) skin discoloration; (iii) numbness of extremities; (iv) shiny skin; (v) small white lumps under the surface of the skin that erupt into a chalky white fluid; (vi) Raynaud's esophagaeal dysfunction; (vii) telangiectasia; (viii) pain and/or stiffness of the joints; (ix) swelling of the hands and feet; (x) itching of the skin; (xi) stiffening and curling of the fingers; (xii) ulcers on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; and (xx) digital auto-amputation.

Another aspect of the invention provides a method for improving the modified Rodnan skin score, reducing or improving the skin thickness, reducing or improving skin induration, improving the pulmonary function, improving the dermatology quality of life index, improving the carbon monoxide diffusing capacity, improving the Mahler Dyspnea index, improving the Saint George's Respiratory Questionnaire score, improving the UCLA scleroderma clinical trial consortium gastrointestinal tract score, improving flow-mediated dilatation, or improving or increasing the six minute walk distance of a patient having scleroderma, comprising administering to the patient an effective amount of a deuterium-enriched compound described herein.

Another aspect of the invention provides a method for modulating activity of a cell selected from the group consisting of a B cell and a T cell, comprising contacting the cell with an effective amount of a deuterium-enriched compound described herein to modulate the activity of the cell.

Another aspect of the invention provides a method for treating an immune-related disorder or a disorder selected from the group consisting of Sjogren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, Degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroiditis), idiopathic pulmonary fibrosis, idiopathic thrombocytopenia purpura, IgA nephropathy, juvenile arthritis, lichen planus, Meniere disease, mixed connective tissue disease, morphea, narcolepsy, neuromyotonia, pediatric autoimmune neuropsychiatric disorders (P AND As), pemphigus vulgaris, pernicious anemia, polyarteritis nodosa, polychondritis, polymyalgia rheumatica, primary agammaglobulinemia, primary biliary cirrhosis, Raynaud's disease (Raynaud's phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and Wegener's granulomatosis. The method comprises administering to a patient in need thereof a therapeutically effective amount of a deuterium-enriched compound described herein to treat the disorder.

Another aspect of the invention provides a method of treating or preventing pain in a subject, comprising administering to a patient in need thereof a therapeutically effective amount of a deuterium-enriched compound described herein. Exemplary types of pain include nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, complex regional pain syndrome (CRPS) type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

Complex regional pain syndrome (CRPS) and CRPS and related syndromes mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Further types of pain contemplated for treatment include, but are not limited to, those described in U.S. patent publication no. 2005/0203142, published Sep. 15, 2005, which is incorporated in its entirety herein by reference.

Examples of macular degeneration (MD) and related syndromes include, but are not limited to, those described in U.S. patent publication no. 2004/0091455, published May 13, 2004, which is incorporated in its entirety herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated in its entirety herein by reference. Specific examples include, but are not limited to, keratoses and related symptoms, skin diseases or disorders characterized with overgrowths of the epidermis, acne, and wrinkles.

"Keratosis" refers to any lesion on the epidermis marked by the presence of circumscribed overgrowths of the horny layer, including but not limited to, actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis"

also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratosis, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratosis, sign of Leser-Trelat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, Cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated in its entirety herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramine, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but are not limited to, those described in U.S. publication no. 2005/0100529, published May 12, 2005, which is incorporated in its entirety herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated in its entirety herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. application Ser. No. 11/289,723, filed Nov. 30, 2005. Specific examples include, but are not limited to, adenosine deaminase deficiency, antibody deficiency with normal or elevated Igs, ataxia-telangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated in its entirety herein by reference. Specific examples include, but are not limited to, amyotrophic lateral sclerosis, Alzheimer's disease, Parkinson's disease, Huntington's disease, multiple sclerosis, other neuroimmunological disorders such as Tourette syndrome, delirium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated in its entirety herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete spinal cord injury (SCI), incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but are not limited to, viral, genetic, allergic, and autoimmune diseases. Specific examples include, but are not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post-ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated in its entirety herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary bypass grafting, angioplasty with stent implantation, peripheral percutaneous transluminal intervention of the iliac, femoral or popliteal arteries, and surgical intervention using impregnated artificial grafts.

The following chart provides a listing of the major systemic arteries that may be in need of treatment, all of which are contemplated herein:

| Artery | Body Areas Supplied |
| --- | --- |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated in its entirety herein by reference. Specific examples include, but are not limited to, snoring, sleep apnea, insomnia, narcolepsy, restless leg syndrome, sleep terrors, sleep walking, sleep eating, and dysfunctional sleep associated with chronic neurological or inflammatory conditions. Chronic neurological or inflammatory conditions, include, but are not limited to, complex regional pain syndrome (CRPS), chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, postherpetic, traumatic or inflammatory), and neurodegenerative disorders such as Parkinson's disease, Alzheimer's disease, amyotrophic lateral sclerosis (ALS), multiple sclerosis, Huntington's disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer's disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; CNS trauma and myoclonus.

Examples of hemoglobinopathy and related disorders include, but are not limited to, those described in U.S. publication no. 2005/0143420A1, published Jun. 30, 2005, which is incorporated in its entirety herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; graft versus host reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, sepsis, endotoxic shock, graft versus host disease, wasting, ulcerative colitis, multiple sclerosis, systemic lupus erythromatosis, ENL in leprosy, HIV, AIDS, and opportunistic infections in AIDS; disorders such as endotoxic shock, hemodynamic shock and sepsis syndrome, post ischemic reperfusion injury, malaria, mycobacterial infection, meningitis, psoriasis, congestive heart failure, fibrotic disease, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other aspects, the use of compounds provided herein in various immunological applications, in particular, as vaccine adjuvants, particularly anticancer vaccine adjuvants, as disclosed in US publication number 2007/0048327, which is incorporated herein in its entirety by reference, is also encompassed. These embodiments also relate to the uses of compounds provided herein in combination with vaccines to treat or prevent cancer or infectious diseases, and other various uses of immunomodulatory compounds such as reduction or desensitization of allergic reactions.

Additional medical disorders for treatment include those described in international patent application publication nos. WO 2012/125459 and WO 2012/125475, each of which is hereby incorporated by reference.

Dosages

Doses of a compound provided herein, or a pharmaceutically acceptable salt, solvate, or stereoisomer thereof, vary depending on factors such as: specific indication to be treated, prevented, or managed; age and condition of a patient; and amount of second active agent used, if any. Generally, a compound provided herein, or a pharmaceutically acceptable salt, solvate, or stereoisomer thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

Second Active Agents

A compound provided herein, or a pharmaceutically acceptable salt, solvate, or stereoisomer thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt, solvate, or stereoisomer thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCl); HER-2 antibodies (such as, for example, trastuzumab (Herceptin®) and pertuzumab (Perjeta®)); VEGFR antibodies (such as, for example, bevacizumab (Avastin®)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; iloinastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; ineterelin; methioninase; metoclopramide; MIF inhibitor; inifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another aspect, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, 2005/0143344, and 2006/0188475.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, COX-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the Physician's Desk Reference 2003. Specific examples include, but are not limited to, salicylic acid acetate (Aspiring), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2-alpha, pentoxifylline, tin etiopurpurin, motexafin lutetium, lucentis, lutetium, 9-fluoro-11,21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hypertension and related disorders include, but are not limited to, anticoagulants, diuretics, cardiac glycosides, calcium-channel blockers, vasodilators, prostacyclin analogues, endothelin antagonists, phosphodiesterase inhibitors (e.g., PDE V inhibitors), endopeptidase inhibitors, lipid-lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2)), epoprostenol (EPO, Floran®), treprostinil (Remodulin®), nitric oxide (NO), bosentan (Tracleer®), amlodipine, prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agents, oblimersen (Genasense®), cis-platinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interferon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levamisole and isoprinosine; biologics such as, but not limited to, gammaglobulin, transfer factor, interleukins, and interferons; hormones such as, but not limited to, thymic hormones; and other immunologic agents such as, but not limited to, B cell stimulators (e.g., BAFF/B1yS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but are not limited to, Levodopa, L-DOPA, cocaine,α-methyl-tyrosine, reserpine, tetrabenazine, benzotropine, pargyline, fenoldopam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine salicylate, physostigmine sulfate, physostigmine bromide, neostigmine bromide, neostigmine methylsulfate, ambenonium chloride, edrophonium chloride, tacrine, pralidoxime chloride, obidoxime chloride, trimedoxime bromide, diacetyl monoxime, pyridostigmine, and demecarium bromide; an anti-inflammatory agent, such as, but not limited to, naproxen sodium, diclofenac sodium, diclofenac potassium, celecoxib, sulindac, oxaprozin, diflunisal, etodolac, ineloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methyl phenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin®, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenoldopam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine salicylate, physostigmine sulfate, physostigmine bromide, neostigmine bromide, neostigmine methylsulfate, ambenonium chloride, edrophonium chloride, tacrine, pralidoxime chloride, obidoxime chloride, trimedoxime bromide, diacetyl monoxime, pyridostigmine, demecarium bromide, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-2 ("rIL2") and canarypox IL-2), IL-10, IL-12, and IL-18; interferons, such as interferon alfa-2a, interferon alfa-2b, interferon alfa-nl, interferon alfa-n3, interferon beta-I a, and interferon gamma-I b; and G-CSF; hydroxyurea; butyrate or butyrate derivatives; nitrous oxide; hydroxyurea; Nicosan (see U.S. Pat. No. 5,800,819); Gardos channel antagonists such as clotrimazole and triaryl methane derivatives; deferoxamine; protein C; and transfusions of blood, or of a blood substitute such as Hemospan® or Hemospan® PS (Sangart).

Administration of a compound provided herein, or a pharmaceutically acceptable salt, solvate, or stereoisomer thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference (60.sup.th ed., 2006).

In another aspect, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but are not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

Cycling Therapy

In certain aspects, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in another aspect, a compound provided herein is administered daily in a single or divided doses in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In yet another aspect, a compound provided herein is administered for a greater number of cycles than would typically cause dose-limiting toxicity in a patient to whom a second active ingredient is not also being administered.

In another aspect, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally, with administration of the compound provided herein occurring 30 to 60 minutes prior to the second active ingredient, during a cycle of four to six weeks. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

The invention may be embodied in other specific forms without departing from the spirit or essential attributes thereof. This invention encompasses all combinations of preferred aspects of the invention noted herein. It is understood that any and all aspects of the invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

PART III. DEFINITIONS

The examples provided in the definitions section as well as the remainder of this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Solvate" means a compound that further includes a stoichiometric or non-stoichiometric amount of solvent bound by non-covalent intermolecular forces. Where the solvent is water, the solvate is a hydrate.

"Alkyl" and "alkylene" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

As noted previously, "alkyl" also includes deuterated alkyl. Each alkyl group contains 2n+1 hydrogen atoms, wherein n=the number of carbon atoms. Deuterated alkyl covers alkyls groups having from 1 to 2n+1 deuteriums. Deuterated $C_{1-6}$ alkyl, for example, includes $C_1$ ($d_{1-3}$), $C_2$ ($d_{1-5}$), $C_3$ ($d_{1-7}$), $C_4$ ($d_{1-9}$) $C_5$ ($d_{1-11}$), and $C_6$ ($d_{1-13}$), alkyl groups.

"Haloalkyl" and "haloalkylene" include alkyl groups as defined above (including deuteration), wherein one or more hydrogens are replaced by a halogen atom selected from Cl, F, Br, and I. Examples of haloalkyl include trifluoromethyl, 1,1,1-trifluoroethyl, and perfluoroethyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

As noted previously, "alkenyl" also includes deuterated alkenyl. Each alkenyl group contains 2(n-i)+1 hydrogen atoms, wherein n=the number of carbon atoms and i=number of double bonds. Deuterated alkenyl covers alkenyls groups having from 1 to 2(n-i)+1 deuteriums. Deuterated $C_{2-6}$ alkenyl, for example, includes $C_2$ ($d_{1-3}$), $C_3$ ($d_{1-5}$), $C_4$ ($d_{1-7}$), $C_5$ ($d_{1-9}$), and $C_6$ ($d_{1-11}$), alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

As noted previously, "alkynyl" also includes deuterated alkynyl. Each alkynyl group contains 2(n-2i)+1 hydrogen atoms, wherein n=the number of carbon atoms and i=number of triple bonds. Deuterated alkenyl covers alkenyls groups having from 1 to 2(n-2i)+1 deuteriums. Deuterated $C_{2-6}$ alkynyl, for example, includes $C_2$ ($d_1$), $C_3$ ($d_{1-3}$), $C_4$ ($d_{1-5}$), $C_5$ ($d_{1-7}$), and $C_6$ ($d_{1-9}$), alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

As noted previously, "cycloalkyl" also includes deuterated cycloalkyl. Each cycloalkyl group contains 2n-1 hydrogen atoms, wherein n=the number of carbon atoms. Deuterated cycloalkyl covers cycloalkyl groups having from 1 to 2n-1 deuteriums. Deuterated $C_{3-8}$ cycloalkyl, for example, includes $C_3$ ($d_{1-5}$), $C_4$ ($d_{1-7}$), $C_5$ ($d_{1-9}$), $C_6$ ($d_{1-11}$), $C_7$ ($d_{1-13}$), and $C_8$ ($d_{1-15}$), cycloalkyl groups.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

As noted previously, "aryl" also includes deuterated aryl. For example, phenyl includes $d_{1-5}$ phenyl.

"Heterocycloalkyl" refers to any stable monocyclic, bicyclic, or tricyclic heterocyclic ring that is non-aromatic, and which consists of the specified number of carbon atoms and 1, 2, 3, or 4 heteroatoms independently selected from the group consisting of N, O, and S. If the heterocycloalkyl group is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms may optionally be oxidized (e.g., S, S(O), S(O)$_2$, and N—O). The heterocycloalkyl ring may be attached to its pendant group at any heteroatom or carbon atom that results in a stable structure. A heterocycloalkyl group can have one or more carbon-carbon double bonds or carbon-heteroatom double bonds in the ring as long as the ring is not rendered aromatic by their presence. The heterocycloalkyl rings described herein may be substituted on carbon or on a nitrogen atom if the resulting compound is stable.

As noted previously, "heterocycloalkyl" also includes deuterated heterocycloalkyl. For example, piperidinyl and piperazino include $d_{1-10}$ piperidinyl or $d_{1-9}$ piperazino.

Examples of heterocycloalkyl include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

As noted previously, "heteroaryl" also includes deuterated heteroaryl. For example, furanyl or thienyl include $d_{1-3}$ furanyl or $d_{1-3}$ thienyl.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Host" preferably refers to a human. It also includes other mammals including the equine, porcine, bovine, feline, and canine families.

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethanedisulfonic, ethanesulfonic, fumaric, glucoheptonic, gluconic, glutamic, glycolic, glycollyarsanilic, hexylresorcinic, hydrobromic, hydrochloric, hydroiodic, hydroxymaleic, hydroxynaphthoic, isethionic, lactic, lactobionic, lauric, laurylsulfonic, maleic, malic, mandelic, methanesulfonic, napsylic, naphthylic, nitric, oleic, oxalic, palmitic, pamoic, pantothenic, phenylacetic, phosphoric, polygalacturonic, propionic, salicylic, stearic, succinic, sulfamic, sulfanilic, sulfuric, tannic, tartaric, toluenesulfonic, and valeric. (See, for example, Berge et al. (1977) "Pharmaceutical Salts", J. Pharm. Sci. 66:1-19.)

"Treat", "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

"Prevent", "preventing" and "prevention" refer to the prevention of the onset, recurrence or spread of a disease or disorder, or of one or more symptoms thereof.

"Manage", "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder.

"Prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Part IV. Exemplary General Procedures for Synthesis of Deuterium-Enriched Compounds The hydrogens present on the 3-(5-substituted-4-oxoquinazolin-3(4H)-yl)-3-deutero-piperidine-2,6-diones have different capacities for exchange with deuterium. For example, hydrogen atom $R^1$ is exchangeable in $H_2O/D_2O$. Hydrogen atoms $R^2$-$R^3$ and the 3-deuterium can be exchanged under basic conditions. The remaining hydrogen atoms are not easily exchangeable for deuterium atoms, though some may be depending on the specific moieties selected for $R^6$ and $R^{10}$. Deuterium atoms at the remaining positions may be incorporated by the use of deuterated starting materials or intermediates via the known synthetic methods for the synthesis of 3-(5-substituted-4-oxoquinazolin-3(4H)-yl)-piperidine-2,6-diones as described in U.S. Pat. No. 7,635,700 (US '700)(e.g., see section 6 starting in Column 41), the contents of which are incorporated in its entirety herein by reference. It is contemplated that the presently described deuteriated 3-(5-substituted-4-oxoquinazolin-3(4H)-yl)-3-deutero-piperidine-2,6-diones can be prepared by incorporating deuterated starting materials into the synthetic route of US '700. Alternatively, deuterium is expected to be incorporated at the exchangeable and acidic positions of the final compound (e.g., $R^{2-3}$ or the 3-position).

Scheme 1 below provides an exemplary synthetic route for preparing deuterated 3-(5-substituted-4-oxoquinazolin-3(4H)-yl)-3-deutero-piperidine-2,6-diones.

SCHEME 1

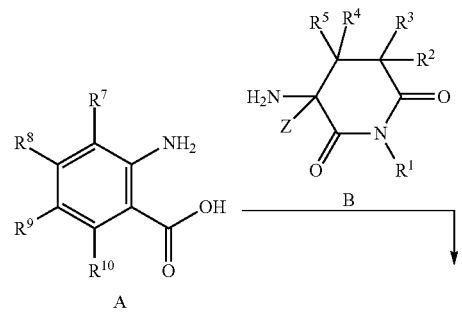

A

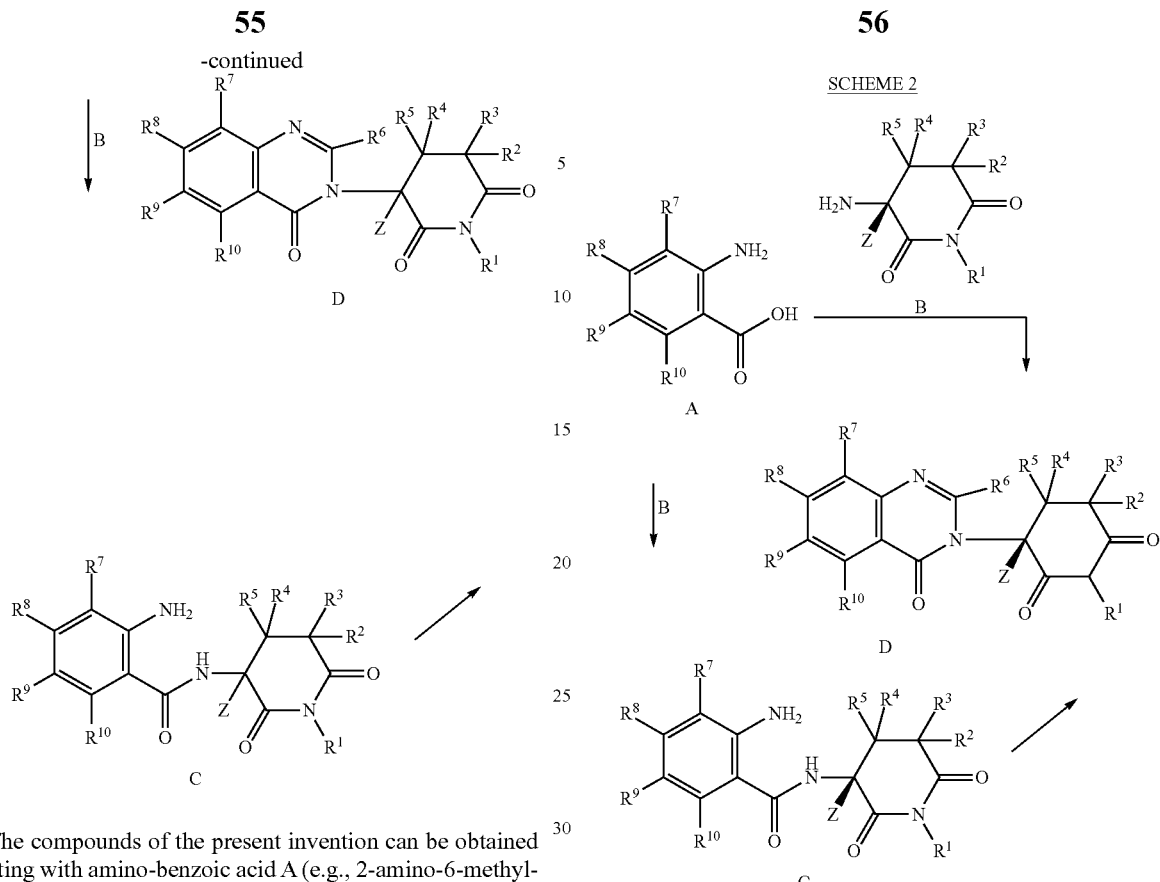

The compounds of the present invention can be obtained starting with amino-benzoic acid A (e.g., 2-amino-6-methyl-benzoic acid), which can be optionally deuterated. When $R^6$=H, one can react compound A with CDI (1,1'-carbonyldiimidazole), followed by the introduction of compound B, which is at least partially deuterated at Z, to yield compound D. Depending on the chosen $R^{10}$, compound D could be further modified.

When Z=H in B, deuterium can be introduced into C or D by contacting either C or D with a base (e.g., NaOD) in the presence of $D_2O$. Chiral chromatography or other known chiral isolation techniques can then be used to resolve the stereoisomers.

Alternatively, when $R^6$ is desired to be other than H, amide C can be formed by reacting A and B. Intermediate C then allows for various $R^6$ groups to be introduced into compound D. For example, triethyl orthoacetate can be used to form compound D, providing $R^6$=CH$_3$. Using triethyl orthoformate-d$_1$ should result in $R^6$=D.

A number of deuterated glutamines (Compound B) have previously been made including 2,3,4-trideutero-glutamine (i.e., $R^2$=D, $R^4$=D, and Z=D), which was made via the deuterium reduction of 6-carboxy-3(2H)-pyridazone (see Stogniew, J. Labelled Compounds and Radiopharmaceuticals 1981, 18(6), 897-903), and 2,2,3,3,4 pentadeuteroglutamine (i.e., $R^2$-$R^5$=D and Z=D), which was obtained in a multi-step synthesis (see Blomquist, J. Org. Chem. 1966, 12, 4121-27). Stogniew also notes that the 5-mono-deuteroglutamine could be obtained through deuterium reduction of 4,5-dihydro-6-carboxy-3(2H)-pyridazone.

If non-stereospecific glutamine is used or if the stereospecificity is lost during the reaction, it is expected that the resulting deuterated racemic mixture will be separable using known isolation techniques (e.g., chiral chromatography).

Scheme 2 below provides an exemplary synthetic route for preparing stereospecific deuterated 3-(5-substituted-4-oxoquinazolin-3(4H)-yl)-3-deutero-piperidine-2,6-diones.

When $R^{10}$ is an amino group or amino derivative, one can arrive at deuterated 3-(5-substituted-4-oxoquinazolin-3(4H)-yl)-3-deutero-piperidine-2,6-diones by starting with a benzo[d][1,3]oxazin-4-one as shown in Scheme 3.

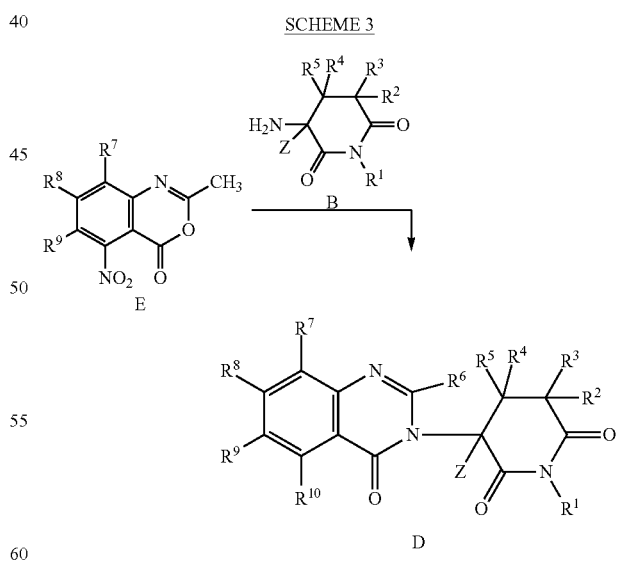

The 5-nitro-2-methyl-benzo[d][1,3]oxazin-4-one, E, can be prepared from 2-amino-6-nitrobenzoic acid and acetic anhydride. Reacting the oxazin-4-one with compound B should provide the nitro-derivative of D. The amine, $R^{10}$=NH$_2$, should be obtained through hydrogenation. Further modification of the amino group can then be made.

When $R^{10}$ is a $(CH_2)_n$-amino moiety, one can use a 6-protected amino starting material as shown in Scheme 4.

SCHEME 4

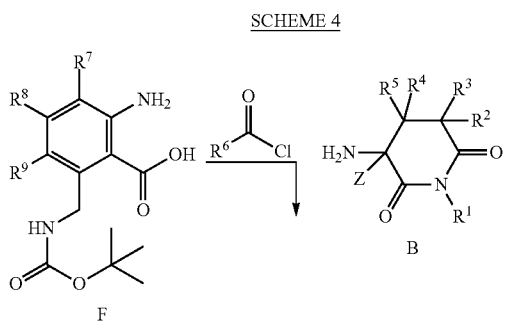

2-amino-6-(tert-butoxycarbonylamino-methyl)-benzoic acid, F, can be made as described in US '700, columns 61-62. F can then be reacted with a carbonyl compound (e.g., acetyl chloride) and the resulting compound reacted with B to arrive at D. The amino protecting group can be removed and further modification of the amine can be performed.

Scheme 5 depicts a route to 5-amino-quinazolinones.

SCHEME 5

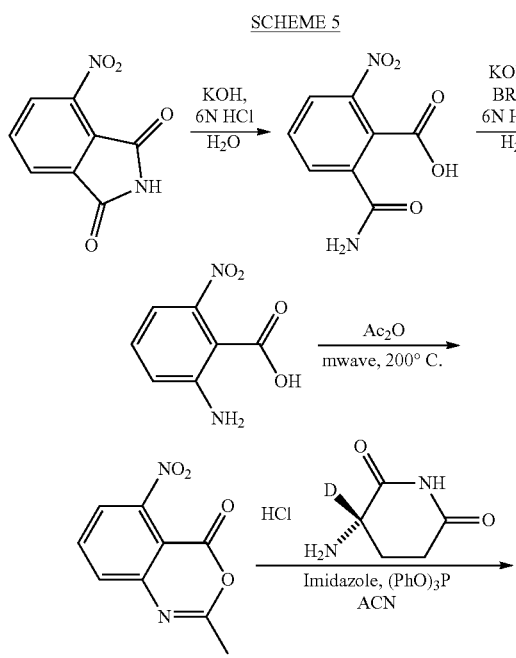

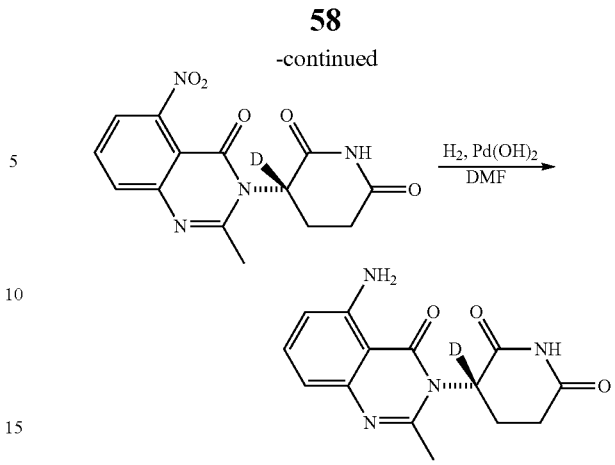

Scheme 6 depicts a route to 5-methyl-quinazolinones.

SCHEME 6

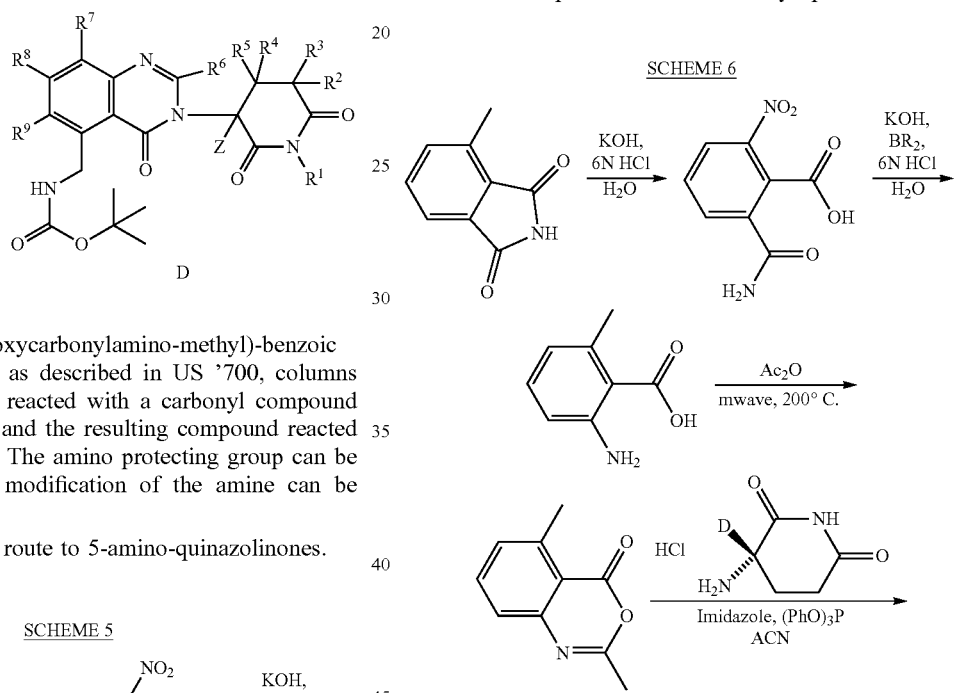

PART V. DOSAGES AND FORMULATIONS

Dosages of a compound provided herein, or stereoisomer or pharmaceutically acceptable salt thereof, vary depending on factors such as: specific indication to be treated and/or managed; age and condition of a patient; and amount of second active agent used, if any. Generally, a compound provided herein, or stereoisomer or pharmaceutically acceptable salt thereof, may be used in an amount of from about 0.1 mg to about 500 mg per day, and can be adjusted in a conventional fashion (e.g., the same amount administered each day of the treatment and/or management period), in cycles (e.g., one week on, one week off), or in an amount that increases or decreases over the course of treatment and/or management. In other aspects, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

Pharmaceutical compositions can be used in the preparation of individual, single unit dosage forms. Pharmaceutical compositions and dosage forms provided herein comprise a compound provided herein, or a pharmaceutically acceptable salt, solvate, or stereoisomer thereof. Pharmaceutical compositions and dosage forms can further comprise one or more excipients.

Pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., Remington's Pharmaceutical Sciences, 18th ed., Mack Publishing, Easton Pa. (1990).

In another aspect of the present invention, the pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but are not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but are not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the present invention provides oral dosage forms that are tablets or capsules, in which case solid excipients are employed. In another aspect, the tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a Syloid® silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the present invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the present invention procies single unit dosage forms suitable for oral administration such as, but are not limited to, tablets, capsules, gelcaps, and caplets that are adapted for controlled-release.

Controlled-release pharmaceutical products improve drug therapy over that achieved by their non-controlled counterparts. In another aspect, the present invention provides the use of a controlled-release preparation in medical treatment characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another aspect, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In another aspect, in order to maintain a constant level of drug in the body, the drug can be released from the dosage form at a rate that will replace the amount of drug being metabolized and excreted from the body. Controlle release of an active ingredient can be stimulated by various conditions including, but are not limited to, pH, temperature, enzymes, water, or other physiological conditions or compounds.

Parenteral dosage forms can be administered to patients by various routes including, but are not limited to, subcutaneous, intravenous (including bolus injection), intramuscular, and intraarterial. Administration of a parenteral dosage form bypasses patients' natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but are not limited to, Sodium Chloride Injection, Ringer's Injection, Dextrose Injection, Dextrose and Sodium Chloride Injection, and Lactated Ringer's Injection; water-miscible vehicles such as, but are not limited to, ethyl alcohol, polyethylene glycol, and polypropylene glycol; and nonaqueous vehicles such as, but are not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are v"+ limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts, solvates, prodrugs, or stereoisomers of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the present invention provides a kit comprising a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL-2, IL-8, IL-18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but are not limited to, Sodium Chloride Injection, Ringer's Injection, Dextrose Injection, Dextrose and Sodium Chloride Injection, and Lactated Ringer's Injection; water-miscible vehicles such as, but are not limited to, ethyl alcohol, polyethylene glycol, and polypropylene glycol; and non-aqueous vehicles such as, but are not limited to, corn oil, cottonseed oil, peanut oil, sesame oil, ethyl oleate, isopropyl myristate, and benzyl benzoate.

EXAMPLES

The invention now being generally described, will be more readily understood by reference to the following examples, which are included merely for purposes of illustration of certain aspects and embodiments of the present invention, and are not intended to limit the invention.

Example 1

Synthesis of rac-3-(5-Amino-2-methyl-4-oxoquinazolin-3(4H)-yl)-(3-²H)-piperidine-2,6-dione Step 1. Synthesis of 2-Methyl-5-nitro-4H-3,1-benzoxazin-4-one

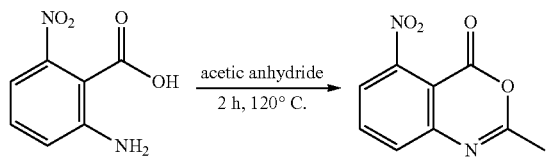

2-Amino-6-nitrobenzoic acid (25.0 g, 137 mmol) was mixed with acetic anhydride (50 mL, 529 mmol) and the resulting mixture was heated to 120° C. by placing the reaction vessel containing this mixture in an oil bath for 2 hours, while monitoring reaction progress by HPLC. Next, the reaction mixture was cooled, and partially concentrated by evaporation under a stream of dry nitrogen. The reaction mixture was then diluted with 100 mL diethyl ether and cooled in a refrigerator overnight. The resulting crystals were filtered and rinsed with diethyl ether (50 mL) to provide the title compound (25.3 g, 123 mmol, 89%) as a tan, crystalline solid. $^1$H NMR (400 MHz, CDCl$_3$) δ 7.91 (t, J=8.0 Hz, 1H), 7.57 (dd, J=7.8, 1.01 Hz, 1H), 7.53 (dd, J=8.3, 1.0 Hz, 1H), 2.53 (s, 3H). MS (ESI+) calc. for [C$_9$H$_6$N$_2$O$_4$+H]$^+$ 207.2. found 207.2.

Step 2. Synthesis of 2-Acetamido-6-nitrobenzoic acid

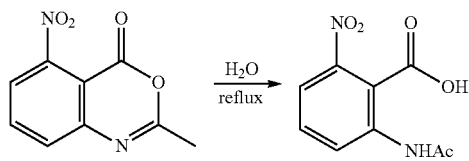 [SMILES: Cc1nc2cccc([N+](=O)[O-])c2c(=O)o1 ; O ; CC(=O)Nc1cccc([N+](=O)[O-])c1C(=O)O]

The starting material (24.7 g, 120 mmol) was dispersed in water (216 mL) and the resulting mixture was heated to reflux for 30 min. Upon cooling the reaction mixture, crystallization began. Next, the reaction mixture was placed in a refrigerator for 18 hours to complete crystallization. The crystalline material was isolated by filtration and dried under vacuum to give the title compound (24.3 g, 108 mmol, 90.5%) as a pale yellow, crystalline solid. $^1$H NMR (300 MHz, MeOH-d$_4$) δ 8.49 (d, J=8.1 Hz, 1H), 8.15 (d, J=7.8 Hz, 1H), 8.01 (t, J=8.2 Hz, 1H), 2.53 (s, 3H). MS (ESI−) calc. for [C$_9$H$_8$N$_2$O$_5$−H]$^-$ 223.0. found 223.1.

Step 3. Synthesis of rac-2-Acetamido-N-(2,6-dioxopiperidin-3-yl)-6-nitrobenzamide

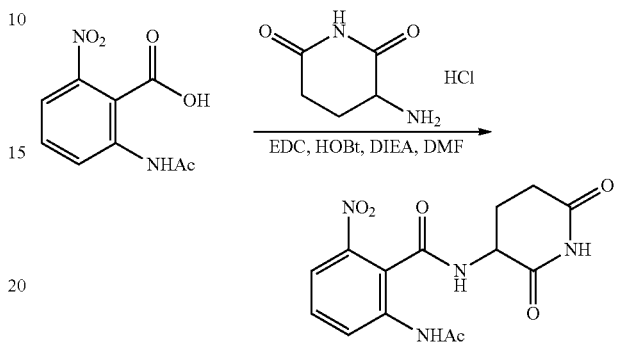

The starting acid (3.10 g, 13.8 mmol) was mixed with hydroxybenzotriazole (HOBt, 2.12 g of the hydrate, 13.8 mmol) and 1-ethyl-3-(3-dimethylaminopropyl)-carbodiimide hydrochloride (EDC, 2.54 g, 13.3 mmol), under a nitrogen atmosphere. N,N-dimethylformamide (DMF, 21.4 mL) was added and the mixture was stirred for 30 minutes at room temperature. rac-3-Aminopiperidine-2,6-dione hydrochloride (5.01 g, 30.4 mmol) was added, followed by N,N-diisopropylethylamine (DIEA, 9.63 mL, 55.3 mmol). The reaction mixture was stirred at 20° C., while monitoring by HPLC. After 24 hours, the reaction mixture showed approximately 40% conversion to the desired product containing some remaining starting acid, but no amine. Then, the reaction mixture was slowly poured into 200 mL water with vigorous stirring. After 20 minutes, a white precipitate began to form. The mixture was placed in the refrigerator for 18 hours. Then, the precipitate was isolated by filtration. The filter cake was washed with 50 mL ether, and air dried to provide the title compound (1.60 g, 4.79 mmol, 35%) as a white powder. $^1$H NMR (300 MHz, DMSO-d$_6$) δ 11.16 (s, 1H), 9.40 (s, 1H), 9.34 (d, J=8.0 Hz, 1H), 8.53 (d, J=7.5 Hz, 1H), 7.89 (dd, J=8.2, 0.98 Hz, 1H), 7.66 (t, J=8.3 Hz, 1H), 4.79 (m, 1H), 2.85 (m, 1H), 2.59 (m, 1H), 2.21 (m, 1H), 2.20 (s, 3H), 2.03 (m, 1H). MS (ESI−) calc. for [C$_{14}$H$_{14}$N$_4$O$_6$−H]$^-$ 333.3. found 333.2.

Step 4. Synthesis of rac-3-(2-Methyl-5-nitro-4-oxoquinazolin-3(4H)-yl)-(3-²H)-piperidine-2,6-dione

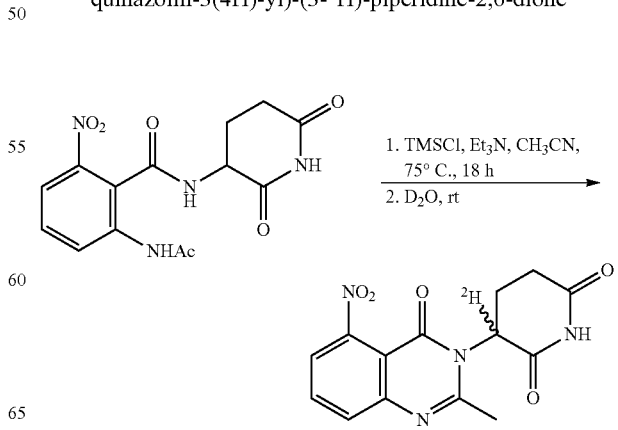

rac-2-Acetamido-N-(2,6-dioxopiperidin-3-yl)-6-nitrobenzamide (4.50 g, 13.5 mmol) was dispersed in anhydrous acetonitrile (70.3 mL) under a nitrogen atmosphere. Triethylamine (88.2 mL, 633 mmol) was added via syringe, followed by the dropwise addition of chlorotrimethylsilane (25.6 mL, 202 mmol). The reaction mixture was warmed to 75° C. and the reaction was monitored by HPLC. After 42 hours, 85% of the desired product was present. The reaction mixture was cooled to 20° C., stirred rapidly, and quenched with deuterium oxide (100 mL, 5.55 moles). The reaction mixture was stirred for an additional 20 minutes and a white precipitate formed. Next, the reaction mixture was cooled in a refrigerator for 4 hours and filtered to provide the title compound (2.25 g, 7.1 mmol, 53%) as an off-white, crystalline solid.

$^1$H NMR (300 MHz, DMSO-$d_6$) δ 11.07 (s, 1H), 7.98 (t, J=7.6 Hz, 1H), 7.83 (2 dd, J=14.4, 8.0, 1.2 Hz, 2H), 2.82 (m, 1H), 2.67 (s, 3H), 2.56 (m, 2H), 2.18 (m, 1H). MS (ESI–) calc. for $[C_{14}H_{11}[^2H]N_4O_5-]^-$ 316.1. found 316.0.

Step 5. Synthesis of rac-3-(5-Amino-2-methyl-4-oxoquinazolin-3(4H)-yl)-(3-$^2$H)-piperidine-2,6-dione

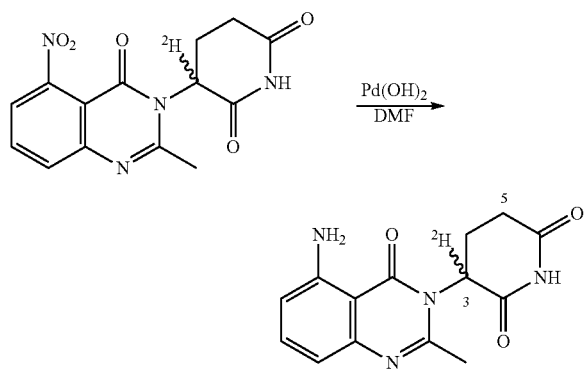

3-(2-Methyl-5-nitro-4-oxoquinazolin-3(4H)-yl)-(3-$^2$H)-piperidine-2,6-dione (2.25 g, 7.09 mmol) was dispersed in DMF (60 mL) in a Parr bottle and palladium hydroxide (500 mg, 20% active catalyst, 50 wt % water) was added. The bottle was then placed under 50 psi hydrogen pressure and shaken for 2 hours at 21° C. The reaction mixture was analyzed by HPLC, which showed a major peak for the desired product and no starting material. The reaction mixture was treated with activated carbon and filtered through a plug of silica gel overlain with 1 cm of sodium sulfate. The plug was washed with 50 mL acetonitrile and the filtrate was evaporated under high vacuum to give a black gum. This material was dissolved in 50 mL of acetonitrile and filtered through a Magnesol® plug, then washed with 100 mL of acetonitrile.

The filtrate was placed in a freezer for 48 hours, and then filtered to afford smoky grey crystals, which were washed with diethyl ether (50 mL) and air dried for 3 hours to give the title compound (1.63 g, 5.67 mmol, 80%). $^1$H NMR (400 MHz, DMSO-$d_6$) δ 10.99 (s, 1H), 7.37 (t, J=8.1 Hz, 1H), 7.03 (br s, 2H), 6.58 (dd, J=11.2, 8.1 Hz, 2H), 2.83 (m, 0.92H), 2.60 (m, 2H), 2.53 (s, 3H), 2.14 (m, 0.92H). MS (ESI+) calc. for $[C_{14}H_{13}[^2H]N_4O_3+H]^-$ 288.1. found 288.2.

$^1$H NMR (400 MHz, pyridine-$d_5$) δ 13.14 (br s, 1H), 7.69 (br s, 2H), 7.46 (t, J=8.1 Hz, 1H), 7.06 (dd, J=7.8, 0.9 Hz, 1H), 6.78 (dd, J=8.2, 0.9 Hz, 1H), 5.39 (dd, J=11.5, 5.7 Hz, 0.06H, residual C(3)H, ca. 94% D incorporation], 3.12 (m, 1H), 2.94 [m, 1.81H, C(5)H, ca. 19% D incorporation], 2.17 (s, 3H), 2.19 (ddd, J=3.2, 4.6, 12.6, 1H).

$^1$H NMR in pyridine-$d_5$ indicates approximately 94% deuterium incorporation at C(3), and approximately 19% deuterium incorporation at C(5). Mass spectroscopic analysis indicates 4% protonated, 80% mono-deuterated, and 16% bis-deuterated.

Example 2

Separation of Pure Enantiomers of rac-3-(5-Amino-2-methyl-4-oxoquinazolin-3(4H)-yl)-piperidine-2,6-dione and Pure Enantiomers of rac-3-(5-Amino-2-methyl-4-oxoquinazolin-3(4H)-yl)-(3-$^2$H)-piperidine-2,6-dione Part I: Separation of Enantiomers from rac-3-(5-Amino-2-methyl-4-oxoquinazolin-3(4H)-yl)-piperidine-2,6-dione rac-3-(5-Amino-2-methyl-4-oxoquinazolin-3(4H)-yl)-piperidine-2,6-dione (136 mg, 0.475 mmol) was dissolved in 10 mL of acetonitrile: isopropanol: methanol (5:3:2 v/v/v). The enantiomers were separated by chiral supercritical fluid chromatography on a ChiralPak AD-H column (21×250 mm) using a mobile phase of 37% isopropanol in carbon dioxide (flow rate: 70 mL/min; 1 mL injected per run). Compounds were detected by UV at 254 nm. Fractions containing the compounds were pooled and evaporated. Purity and enantiomeric excess (% ee=% enantiomer 1-% enantiomer 2) were determined by analytical supercritical fluid chromatography on a ChiralPak AD-H column (4.6× 100 mm) using the same eluent. The enantiomers, peaks 1 and 2, identified as (−)-3-(5-amino-2-methyl-4-oxoquinazolin-3(4H)-yl)-piperidine-2,6-dione and (+)-3-(5-amino-2-methyl-4-oxoquinazolin-3(4H)-yl)-piperidine-2,6-dione, respectively, were dried under vacuum and stored in the freezer. Yield: 134.1 mg overall (0.468 mmol, 98.6%) as 67.3 mg peak 1 (0.235 mmol, 99.7% purity and 99.4% ee) and 66.8 mg peak 2 (0.233 mmol, 99.8% purity and 99.6% ee).

Part II: Separation of Enantiomers from rac-3-(5-Amino-2-methyl-4-oxoquinazolin-3 (4H)-yl)-(3-$^2$H)-piperidine-2,6-dione The enantiomers of rac-3-(5-amino-2-methyl-4-oxoquinazolin-3(4H)-yl)-(3-2H)piperidine-2,6-dione were separated using the chromatographic method described in Part I above. Separation of 0.948 g of rac-3-(5-amino-2-methyl-4-oxoquinazolin-3(4H)-yl)-(3-$^2$H)piperidine-2,6-dione (3.3 mmol) gave the two pure enantiomers in 726.7 mg (2.53 mmol, 77%) overall yield. Purity and enantiomeric excess were determined by supercritical fluid analytical chromatography as described above. Deuterium content was measured by LC/MS-MS and optical rotation was measured in N,N-dimethylformamide (DMF) at room temperature.

(−)-3-(5-Amino-2-methyl-4-oxoquinazolin-3(4H)-yl)-(3-²H)piperidine-2,6-dione 340 mg (1.18 mmol); 99.8% purity; 99.6% ee; LC-MS: 288.3 (M+1) (90.3% deuterium); ¹H NMR (200 MHz, DMSO-d₆) δ 10.95 (s, 1H), 7.33 (t, J=8 Hz, 1H), 6.99 (br s, 2H), 6.56 (d, J=8 Hz, 1H), 6.52 (d, J=6 Hz, 1H), 5.1 (m, 0.12H, residual C(3)H, approximately 88% deuterium incorporation), 2.75 (m, 6H), 2.11 (m, 1H); optical rotation $[\alpha]_D = -47.2°$ (c 1.0, 19.3° C., DMF).

(+)-3-(5-Amino-2-methyl-4-oxoquinazolin-3(4H)-yl)-(3-²H)piperidine-2,6-dione 386.7 mg (1.35 mmol); 99.2% purity; 98.4% ee; LC-MS: 288.3 (M+1) (92.6% deuterium); ¹H NMR (300 MHz, DMSO-d₆) δ 11.04 (s, 1H), 7.40 (t, J=8.0 Hz, 1H), 7.0 (br s, 2H), 6.61 (d, J=8.0, 2H), 5.2 (m, 0.14H, residual C(3)H, approximately 86% deuterium incorporation), 2.82 (m, 1H), 2.61 (m, 5H), 2.15 (m, 1H); optical rotation $[\alpha]_D = +43.35°$ (c 1.0, 19.3° C., DMF).

Example 3

Mouse and Human Plasma Stability of (+)-3-(5-Amino-2-methyl-4-oxoquinazolin-3(4H)-yl)-piperidine-2,6-dione, (−)-3-(5-Amino-2-methyl-4-oxoquinazolin-3(4H)-yl)-piperidine-2,6-dione, and rac-3-(5-Amino-2-methyl-4-oxoquinazolin-3(4H)-yl)-(3-H)-piperidine-2,6-dione (+)- and (−)-3-(5-Amino-2-methyl-4-oxoquinazolin-3(4H)-yl)-piperidine-2,6-dione and rac-3-(5-amino-2-methyl-4-oxoquinazolin-3(4H)-yl)-(3-²H)-piperidine-2,6-dione (87% deuterium content at the C3-position and no detectable deuterium at the C5-position, 50:50 racemic mixture of (+)- and (−)-deuterated enantiomers) were incubated in CD-1 mouse plasma (K₃EDTA as anticoagulant) or human plasma (K₃EDTA as anticoagulant) at 37° C. in duplicates. Aliquots were removed at t=0, 0.5, 1, 2, 6, 8, 24, 48, and 96 h.

Plasma proteins were precipitated by addition of acetonitrile containing internal standard (ISTD, tolbutamide) and the supernatants were analyzed semi-quantitatively by LC/MS-MS with elution on a chiral column (Daicel ChiralPak IE-3) for the separation of enantiomers (isocratic method of 20:80 v/v 0.1% acetic acid in water and acetonitrile). Peak areas for the deuterated enantiomers (+)- and (+3-(5-amino-2-methyl-4-oxoquinazolin-3(4H)-yl)-(3-²H)-piperidine-2,6-dione were normalized to the ISTD and corrected for the isotopic peak of the corresponding protonated enantiomer, (+)- and (+3-(5-amino-2-methyl-4-oxoquinazolin-3(4H)-yl)-piperidine-2,6-dione respectively, if present. Corrected data were analyzed and plotted using Microsoft Excel 2013 (Microsoft Corp, Redmond, Wash.) and the Excel Solver.

Scheme 1 below illustrates the possible reactions in a solution of deuterated racemate. The deuterium in both enantiomers, d+ and d−, can be lost by D/H exchange to give both protonated enantiomers, h+ and h− with rate constants $k_{D++}$, $k_{D+-}$, $k_{D-+}$, $k_{D--}$. At the same time, the protonated enantiomers h+ and h−, can exchange, with enantiomerization rate constants $k_{+-}$ and $k_{-+}$. All four compounds can also degrade with potentially different degradation rate constants $k_{h+d}$, $k_{h-d}$, $k_{d+d}$, $k_{d-d}$.

Scheme 1: Illustration of possible reactions and corresponding rate constants in a solution of rac-3-(5-amino-2-methyl-4-oxoquinazolin-3(4H)-yl)-(3-²H)-piperidine-2,6-dione where d+, d-, h+, h- stand for (+)- and (-)-3-(5-amino-2-methyl-4-oxoquinazolin-3(4H)-yl)-(3-²H)-piperidine-2,6-dione and (+)- and (-)-3-(5-amino-2-methyl-4-oxoquinazolin-3(4H)-yl)-piperidine-2,6-dione, respectively.

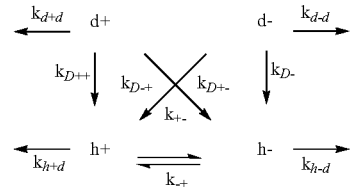

Human and mouse plasma data were analyzed independently. Independent analyses of the data for h+ and h− were performed first and the average rate constants $k_{+-}$ and $k_{-+}$ from these two fits were calculated and used as constants in the fitting of the stability data of the deuterated racemate. Calculated concentrations were obtained through numerical approximation of differential equations (1) and (2) for the stability studies of h+ and h− and equations (3) to (6) for the stability study of deuterated racemate (50:50 d+:d−) by the Euler method (equation (7)). The step between calculated time points was minimized in order to minimize the local error (proportional to the square of the step size) and the global error (proportional to the step size).

To limit the complexity of calculations, the assumption was made that degradation was not affected by the isotopic substitution or the chirality, hence $k_{h+d} = k_{h-d} = k_{d+d} = k_{d-d} = k_d$. The average degradation rate constant obtained by fitting the data for h+ and h− was used in the fit of the stability data of the deuterated racemate. Data analysis was performed in Microsoft Excel 2013, using the Solver Generalized Reduced Gradient Nonlinear method with central derivatives to minimize the sum of sums of weighted $\Delta^2$, square of difference between ISTD-normalized experimental data and calculated value, divided by the experimental data.

$$\frac{d[h+]}{dt} = -(k_{+-} + k_d)[h+] + k_{-+}[h-]$$ Equations 1-6

$$\frac{d[h-]}{dt} = k_{+-}[h+] - (k_{-+} + k_d)[h-]$$

$$\frac{d[h+]}{dt} = -(k_{+-} + k_d)[h+] + k_{-+}[h-] + k_{D++}[d+] + k_{D-+}[d-]$$

$$\frac{d[h-]}{dt} = k_{+-}[h+] - (k_{-+} + k_d)[h-] + k_{D+-}[d+] + k_{D--}[d-]$$

$$\frac{d[d+]}{dt} = -(k_{D++} + k_{D+-} + k_d)[d+]$$

$$\frac{d[d-]}{dt} = -(k_{D--} + k_{D-+} + k_d)[d-]$$

where [h+], [h−], [d+], [d−] are the concentrations of both protonated and deuterated enantiomers, $k_{+-}$ and $k_{-+}$ are the rate constants for the enantiomerization reactions [h+] to [h−] and [h−] to [h+] respectively, $k_{D++}$, $k_{D+-}$, $k_{D-+}$, and $k_{D--}$ are the rate constants for the D/H exchange reactions [d+] or

[d−] to [h+] or [h−], and $k_d$ is the rate constant for the degradation of all four compounds $$[X]_{t2}=[x]_{t1}+(t_2-t_1)[d[X]]_{t1} \quad \text{Equation 7}$$

where $[X]_{ti}$ is the concentration of either enantiomer at time ti, t1 is a time at which [X] is known, t2 is a time at which [X] is calculated, and $[d[X]]_{t1}$ is the calculated value of the differential equation at time t1.

Figure 2:
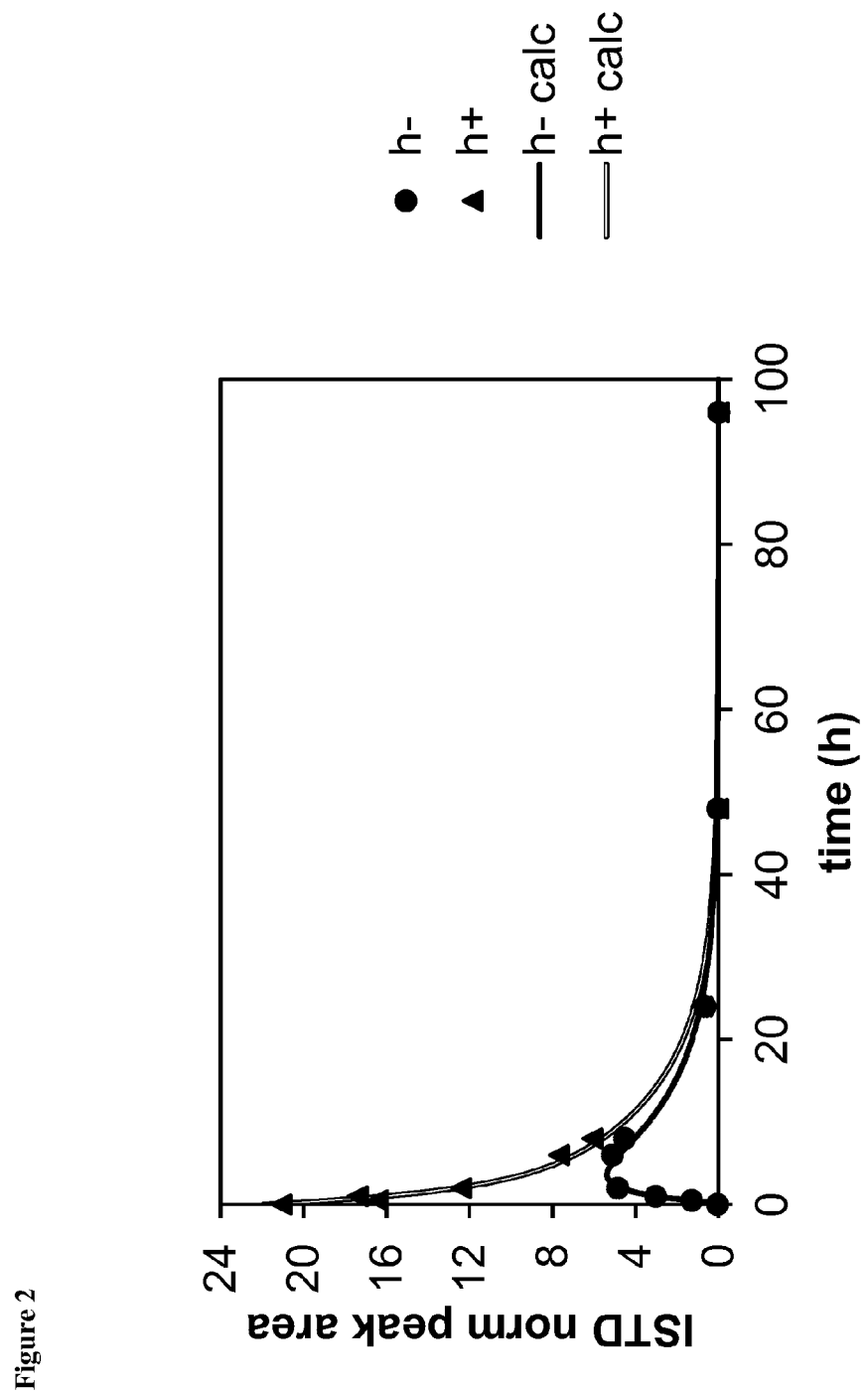
FIG. 2 is a graph showing in vitro stability data for (+)-3-(5-amino-2-methyl-4-oxoquinazolin-3(4H)-yl)-piperidine-2,6-dione (designated "h+") in human plasma, as described in Example 3, where the abbreviation "calc" indicates results from fitting experimental data to kinetic differential equations.
Figure 3:
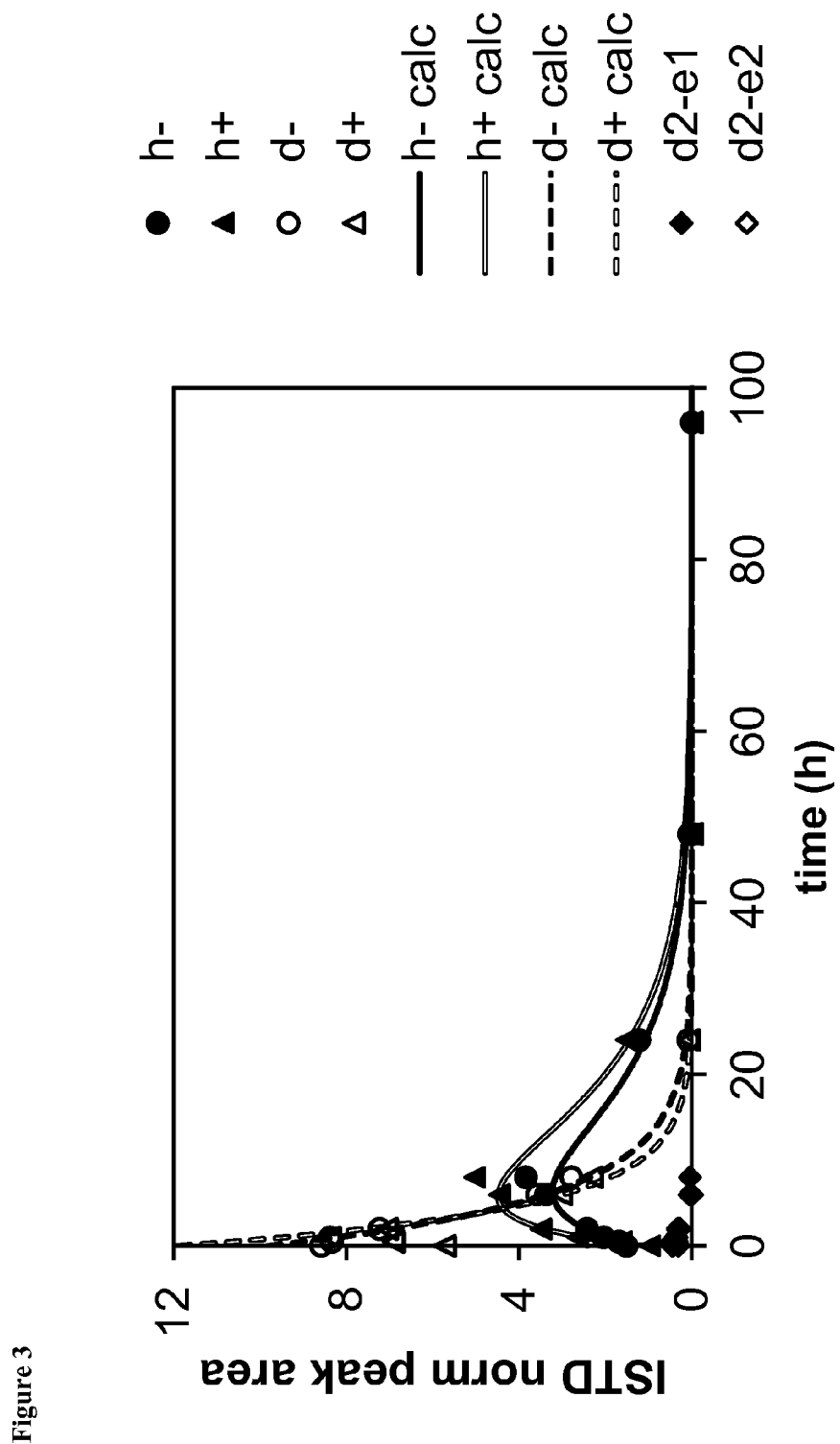
FIG. 3 is a graph showing in vitro stability data for racemic 3-(5-amino-2-methyl-4-oxoquinazolin-3(4H)-yl)-(3-$^2$H)-piperidine-2,6-dione (which is a 1:1 mixture of the (−)-deuterated enantiomer (i.e., "d-") and (+)-deuterated enantiomer (i.e., "d+") and which is designated "d-rac") in human plasma, as described in Example 3. The abbreviations d2-e1 and d2-e2 correspond to a low amount of the enantiomers of 3,5-bis-deuterated 3-(5-amino-2-methyl-4-oxoquinazolin-3(4H)-yl)-piperidine-2,6-dione. The abbreviation "calc" indicates results from fitting experimental data to kinetic differential equations.
Figure 4:
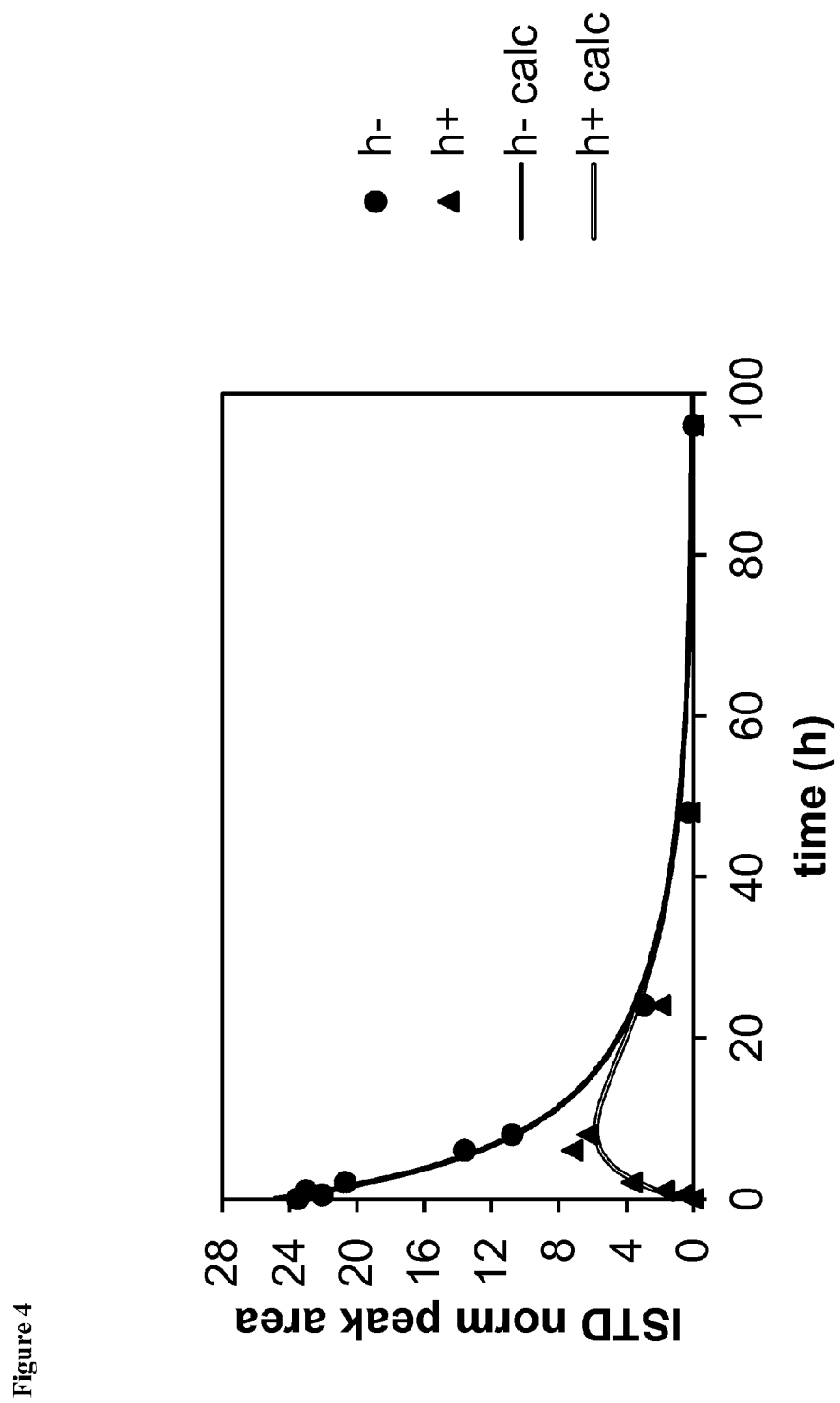
FIG. 4 is a graph showing in vitro stability data for (−)-3-(5-amino-2-methyl-4-oxoquinazolin-3(4H)-yl)-piperidine-2,6-dione (designated "h-") in mouse plasma, as described in Example 3, where the abbreviation "calc" indicates results from fitting experimental data to kinetic differential equations.
Figure 5:
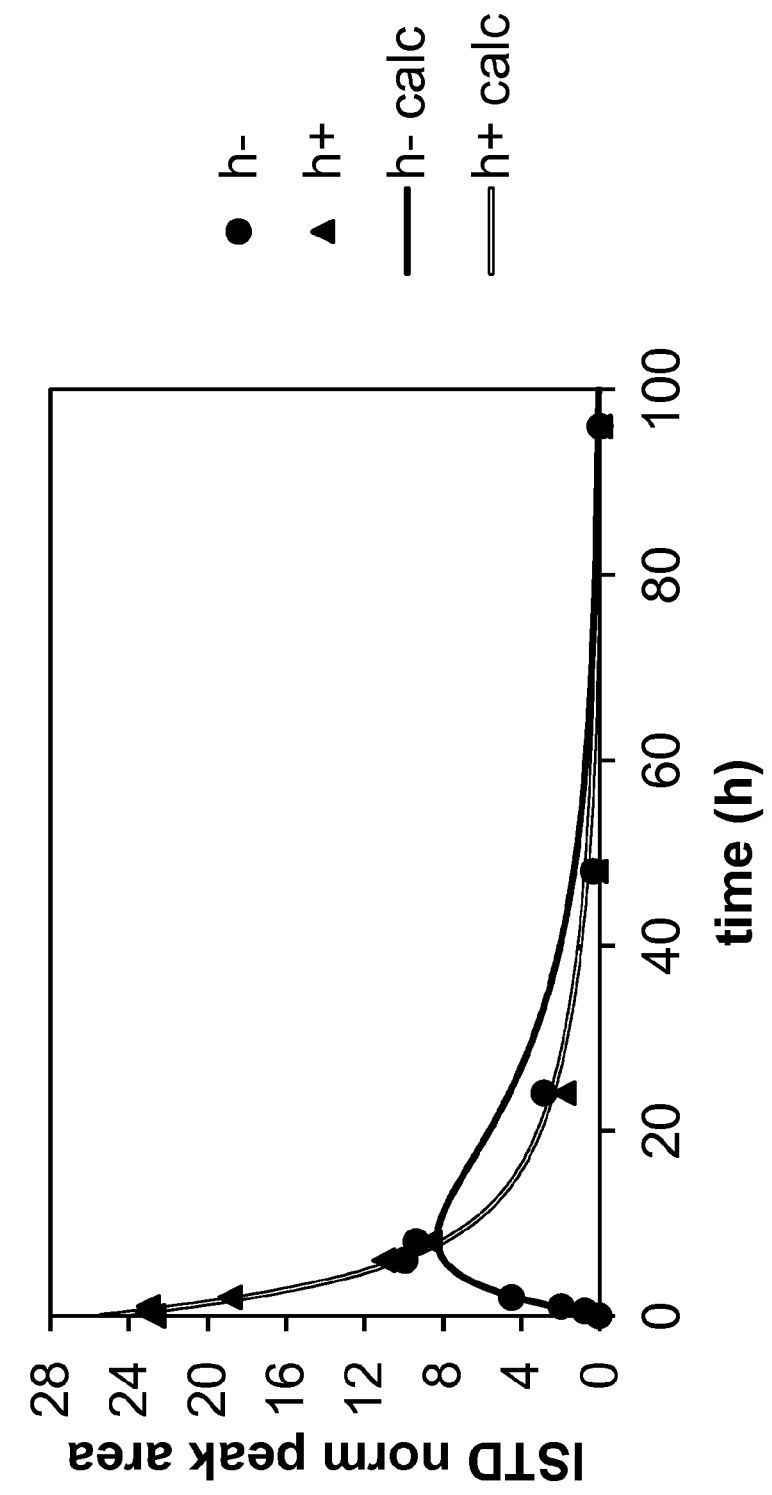
FIG. 5 is a graph showing in vitro stability data for (+)-3-(5-amino-2-methyl-4-oxoquinazolin-3(4H)-yl)-piperidine-2,6-dione (designated "h+") in mouse plasma, as described in Example 3, where the abbreviation "calc" indicates results from fitting experimental data to kinetic differential equations.
Figure 6:
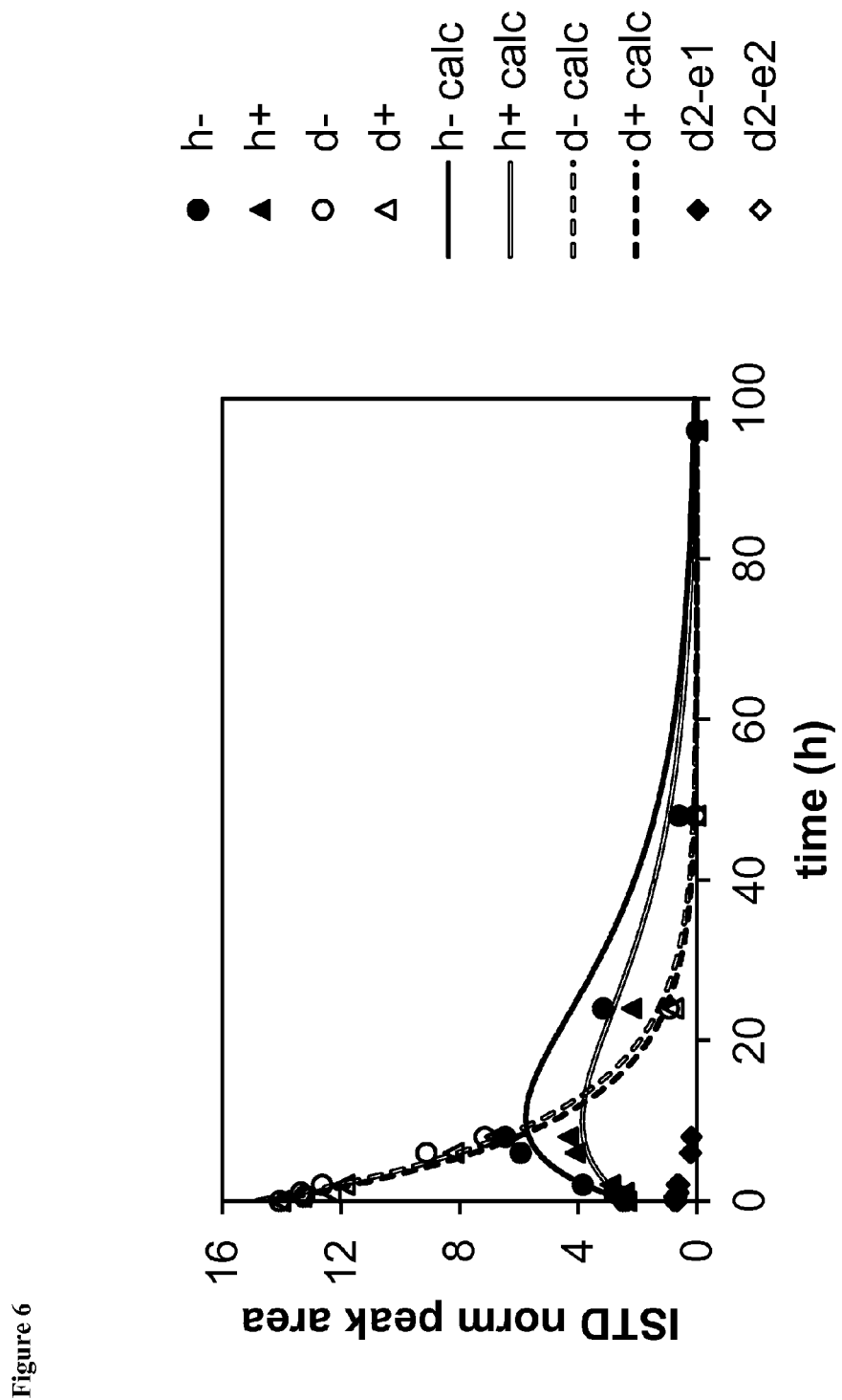
FIG. 6 is a graph showing in vitro stability data for racemic 3-(5-amino-2-methyl-4-oxoquinazolin-3(4H)-yl)-(3-$^2$H)-piperidine-2,6-dione (which is a 1:1 mixture of the (−)-deuterated enantiomer (i.e., "d−") and (+)-deuterated enantiomer (i.e., "d+") and which is designated "d-rac") in mouse plasma, as described in Example 3. The abbreviation d2-e1 and d2-e2 correspond to a low amount of the enantiomers of 3,5-bis-deuterated 3-(5-amino-2-methyl-4-oxoquinazolin-3(4H)-yl)-piperidine-2,6-dione. The abbreviation "calc" indicates results from fitting experimental data to kinetic differential equations.

The observed and fitted data are shown in FIGS. 1-3 for human plasma. The observed and fitted data are shown in FIGS. 4-6 for mouse plasma. Fitted parameters are presented in Table 1.

polation on standard curves prepared in mouse plasma using standard solutions of the analytes.

Figure 7:
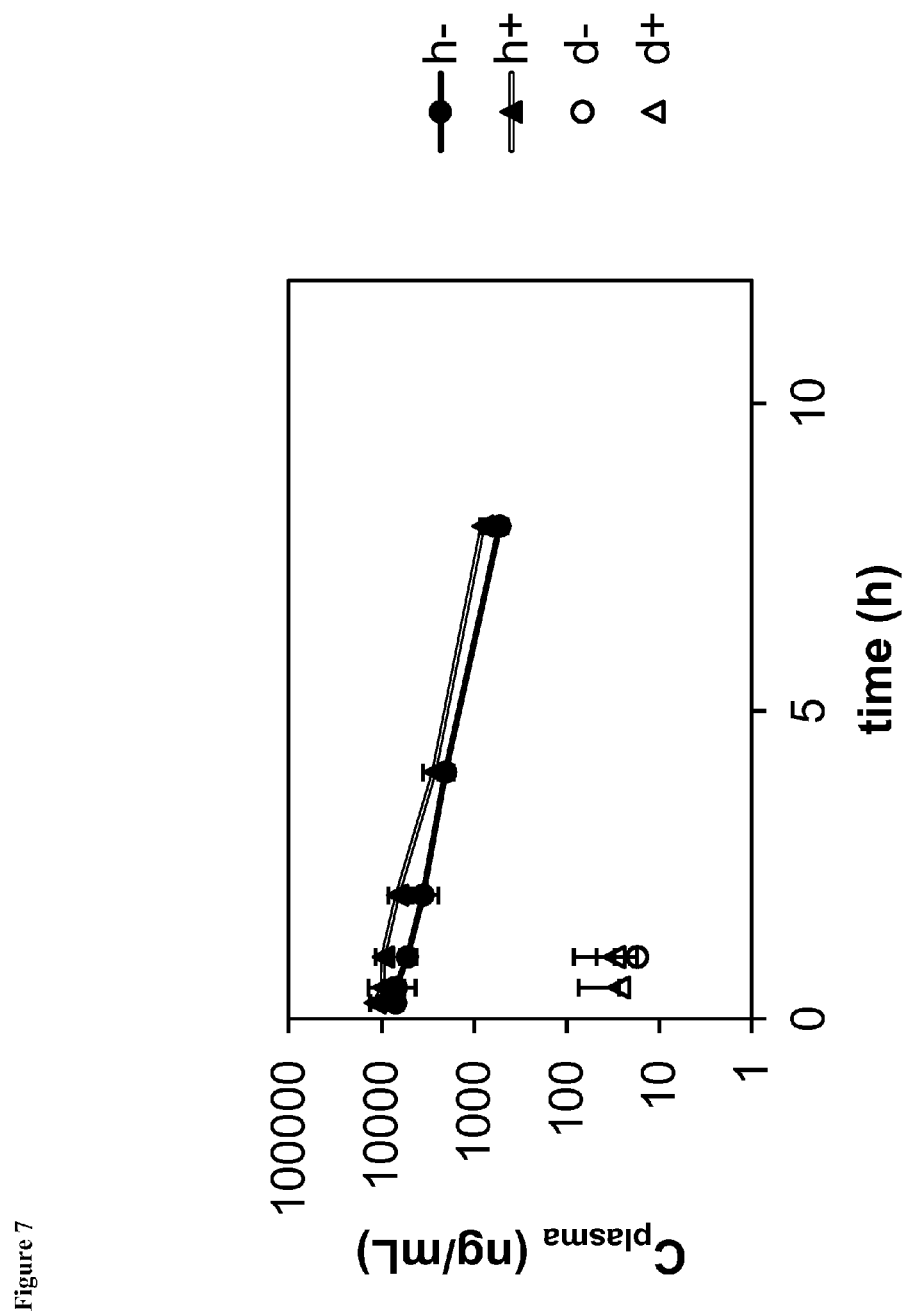
FIG. 7 is a graph of plasma concentration of rac-3-(5-amino-2-methyl-4-oxoquinazolin-3(4H)-yl)-piperidine-2,6-dione (i.e., a 1:1 mixture of the (−)-enantiomer (abbreviated "h−") and the (+)-enantiomer (abbreviated "h+")) following oral administration of rac-3-(5-amino-2-methyl-4-oxoquinazolin-3(4H)-yl)-piperidine-2,6-dione (30 mg/kg) to mice, as described in Example 4.
Figure 8:
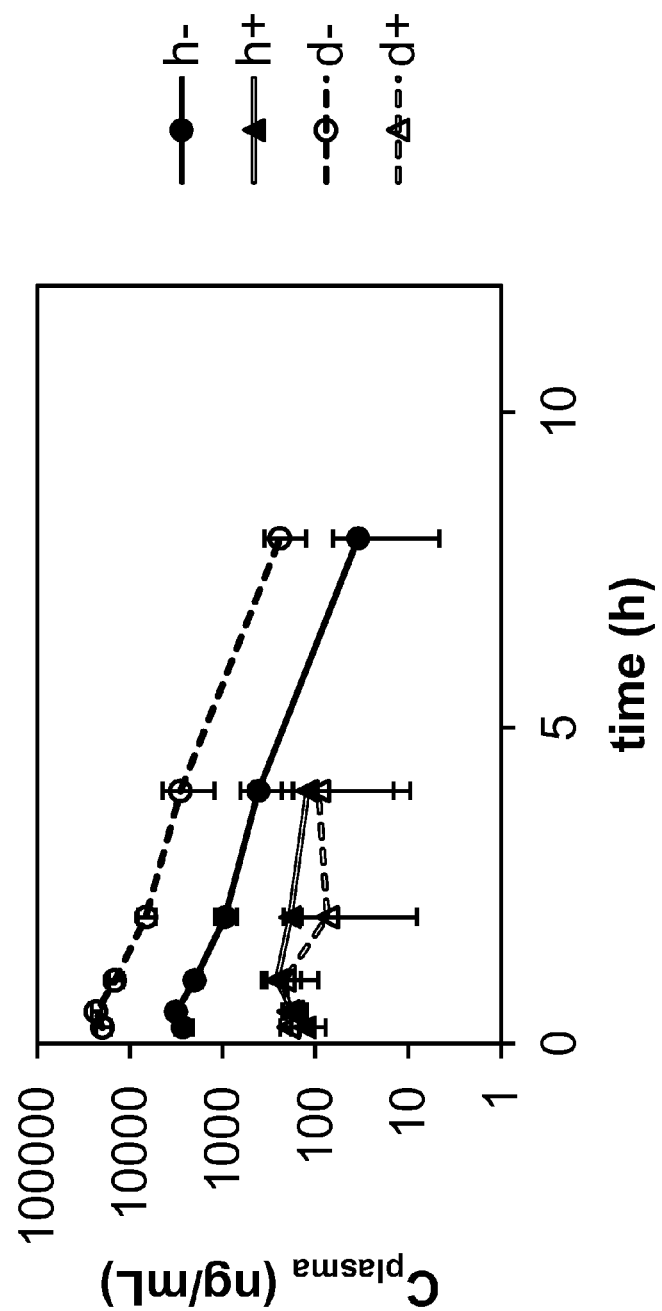
FIG. 8 is a graph of plasma concentration of (−)-3-(5-amino-2-methyl-4-oxoquinazolin-3(4H)-yl)-(3-$^2$H)-piperidine-2,6-dione (abbreviated "d−") following oral administration of (−)-3-(5-amino-2-methyl-4-oxoquinazolin-3(4H)-yl)-(3-$^2$H)-piperidine-2,6-dione (15 mg/kg) to mice, as described in Example 4.
Figure 9:
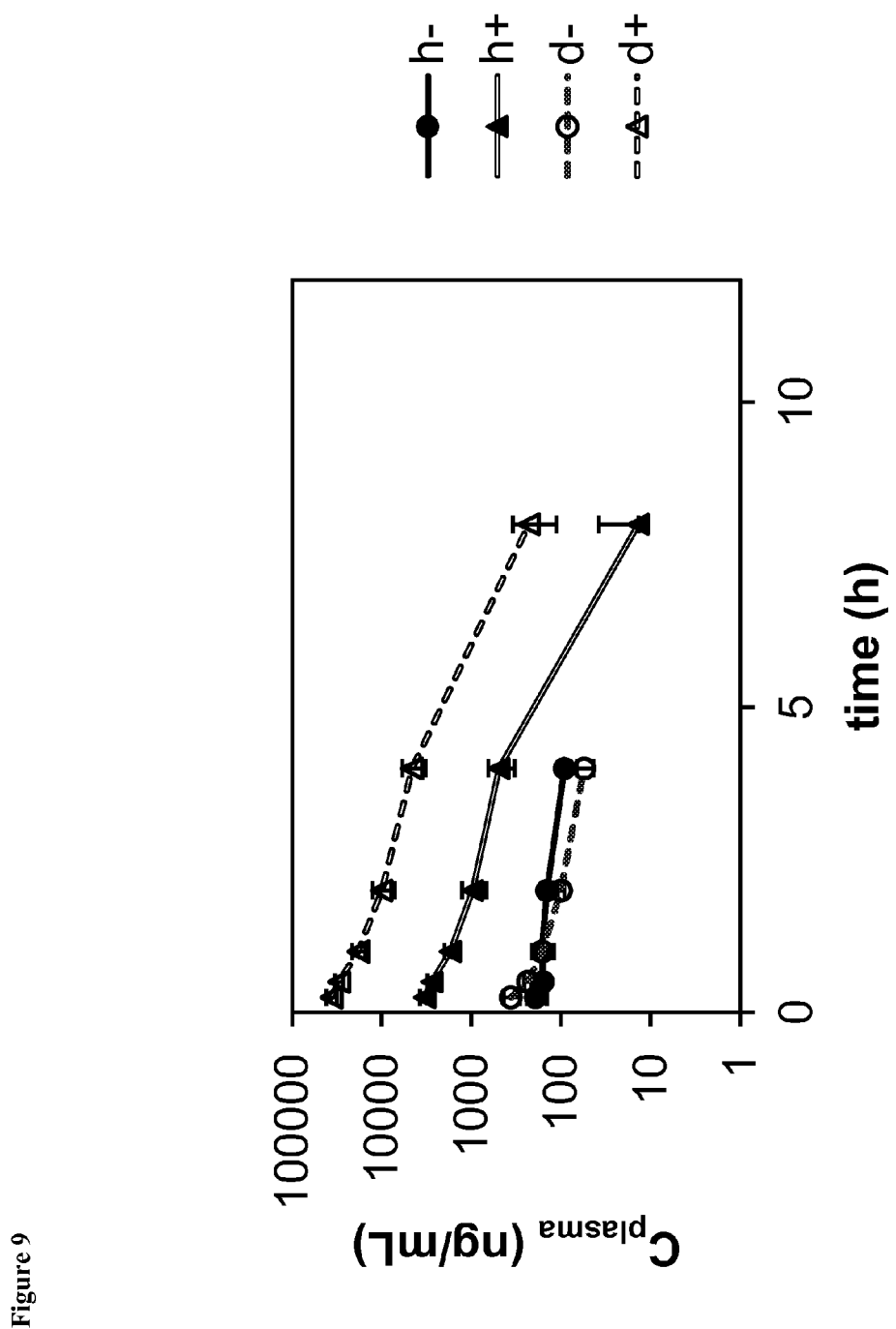
FIG. 9 is a graph of plasma concentration of (+)-3-(5-amino-2-methyl-4-oxoquinazolin-3(4H)-yl)-(3-$^2$H)-piperidine-2,6-dione (abbreviated "d+") following oral administration of (+)-3-(5-amino-2-methyl-4-oxoquinazolin-3(4H)-yl)-(3-$^2$H)-piperidine-2,6-dione (15 mg/kg) to mice, as described in Example 4.

Data was plotted in Excel 2013 (Microsoft Corp, Redmond, Wash.) and analyzed within Excel using the PKSolver add-in (version 2.0, as described in Zhang Y. et at Comput. Methods Programs Biomed. 99 (2010), 306-314) to determine pharmacokinetic parameters including exposure (as area under the curve, AUC) and elimination half-life ($t_{1/2}$). Pharmacokinetic profiles are shown in FIGS. 7-9 and selected pharmacokinetic parameters are presented in Table 1 below.

TABLE 1

Rate Constants and Calculated Half-life ($t_{1/2}$) for the In Vitro Stability of h−, h+, and d-rac in Human and Mouse Plasma at 37° C. Obtained by Fitting Experimental Data to Equations 1 to 6.

| Species | Compound | | D++ | D+− | D−+ | D−− | +−* | −+* | d** |
|---|---|---|---|---|---|---|---|---|---|
| human | d-rac | k (h$^{-1}$) | 0.084 | 0 | 0 | 0.134 | 0.264 | 0.195 | 0.0905 |
| | | $t_{1/2}$ (h) | | 8.3 | | 5.2 | 2.6 | 3.6 | 7.8 |
| | h− | k (h$^{-1}$) | — | — | — | — | 0.231 | 0.169 | 0.0845 |
| | | $t_{1/2}$ (h) | | — | | — | 3.0 | 4.1 | 8.2 |
| | h+ | k (h$^{-1}$) | — | — | — | — | 0.297 | 0.220 | 0.0965 |
| | | $t_{1/2}$ (h) | | — | | — | 2.3 | 3.2 | 7.2 |
| mouse | d-rac | k (h$^{-1}$) | 0.0466 | 0.00109 | 0.0166 | 0.0380 | 0.0662 | 0.0959 | 0.0533 |
| | | $t_{1/2}$ (h) | | 14.5 | | 12.7 | 10.5 | 7.2 | 13.0 |
| | h− | k (h$^{-1}$) | — | — | — | — | 0.0722 | 0.0730 | 0.0544 |
| | | $t_{1/2}$ (h) | | — | | — | 9.6 | 9.5 | 12.7 |
| | h+ | k (h$^{-1}$) | — | — | — | — | 0.0603 | 0.119 | 0.0523 |
| | | $t_{1/2}$ (h) | | — | | — | 11.5 | 5.8 | 13.3 |

*enantiomerization rate constants used in analysis of stability of deuterated racemate d-rac = average of enantiomerization rate constants obtained by fitting data for stability of h− and h+.
**degradation rate constant for the enantiomers of d-rac = average of degradation rate constants for h− and h+.

Example 4

Pharmacokinetics of rac-3-(5-Amino-2-methyl-4-oxoquinazolin-3(4H)-yl)-piperidine-2,6-dione (abbreviated "h-rac"), (+)-3-(5-Amino-2-methyl-4-oxoquinazolin-3(4H)-yl)-(3-$^2$H)-piperidine-2,6-dione (abbreviated "d+"), and (−)-3-(5-Amino-2-methyl-4-oxoquinazolin-3(4H)-yl)-(3-$^2$H)-piperidine-2,6-dione (abbreviated "d-"

Female CB.17 SCID mice (8-12 weeks of age) were administered a single dose of protonated racemate (h-rac, 30 mg/kg), d− (15 mg/kg), or d+ (15 mg/kg) by oral gavage. Deuterated enantiomers (i.e., d− and d+) used in this study contain ~10% of the corresponding protonated enantiomer. Blood was collected into potassium EDTA (K$_2$EDTA) containers by terminal cardiac puncture under carbon dioxide anesthesia from N=3 per group per time point at 0.25, 0.5, 1, 2, 4, 8, and 24 h post-dose. Plasma was isolated, frozen, and stored until ready for analysis.

Samples were prepared for quantitative analysis by liquid-liquid extraction in methyl-t-butylether (MTBE) with ondansetron as internal standard (ISTD). MTBE was evaporated under nitrogen flow and samples were reconstituted in 1% acetic acid in water/acetonitrile (20/80). Analysis was performed by chiral LC/MS-MS on a Daicel ChiralPak IE-3 column using an isocratic LC method of 0.1% acetic acid in water and acetonitrile (20:80 v/v). ISTD-normalized peak areas for deuterated enantiomers d− and d+ were corrected from interference from naturally occurring isotopes of the protonated analytes. Concentrations were obtained by inter-

TABLE 1

Select Pharmacokinetic (PK) Parameters for Enantiomers of Protonated and Deuterated 3-(5-Amino-2-methyl-4-oxoquinazolin-3(4H)-yl)-piperidine-2,6-dione.

| | | Compound Administered by Oral Gavage (dosage) | | |
|---|---|---|---|---|
| Compound Analyzed | PK Parameter | h-rac (30 mg/kg) | d− (15 mg/kg) | d+ (15 mg/kg) |
| h− | $t_{1/2}$ (h) | 2.1 | 1.2 | N/A |
| | AUC (ng · h/mL) | 22500 | 6160 | 993 |
| h+ | $t_{1/2}$ (h) | 2.0 | N/A | 1.0 |
| | AUC (ng · h/mL) | 35900 | 1180 | 6120 |
| d− | $t_{1/2}$ (h) | — | 1.2 | N/A |
| | AUC (ng · h/mL) | — | 44100 | 661 |
| d+ | $t_{1/2}$ (h) | — | N/A | 1.1 |
| | AUC (ng · h/mL) | — | 898 | 63600 |

The experimental results indicate that elimination is fast ($t_{1/2}$=1-2 h) for both protonated and deuterated enantiomers of 3-(5-amino-2-methyl-4-oxoquinazolin-3(4H)-yl)-piperidine-2,6-dione, irrespective of chirality. Exposure to the enantiomers of the protonated molecule is stereoselective with h− representing 39% of the total exposure. Exposure to the deuterated enantiomers shows the same stereoselectivity. Exposure to the protonated enantiomers h− and h+ upon administration of the deuterated enantiomers represents about 10-14% of the total exposure, corresponding to the amount of protonated compound in the dosed material. Little to no D/H exchange is evidenced in the pharmacokinetic parameters, and exposure to the dosed enantiomer (protonated and deuterated) represents 96-98% of the total exposure.

Example 5

Efficacy of (+)-3-(5-Amino-2-methyl-4-oxoquinazolin-3(4H)-yl)-(3-$^2$H)-piperidine-2,6-dione (abbreviated "d+") and (−)-3-(5-Amino-2-methyl-4-oxoquinazolin-3(4H)-yl)-(3-$^2$H)-piperidine-2,6-dione (abbreviated "d-") in Human Multiple Myeloma H929 Cell Line in Female CB.17 SCID Mice Female CB.17 SCID mice (8-12 weeks of age, N=60) were administered 1×10$^7$ H929 tumor cells in 50% Matrigel subcutaneously in their flank (0.2 mL/mouse). Animals were returned to their cages and tumor growth was monitored. Tumor size was reported as tumor volume (Vol) calculated as Vol=½ (L*W$^2$), where L and W are the length and width of the tumor as measured by caliper (L>W). A pair match was performed when tumors reached an average size of 100-150 mm$^3$ and the animals were divided into 6 treatment groups of N=10 animals each.

Animals were treated daily by oral gavage (10 mL/kg) with vehicle, d− (1.5 or 15 mg/kg), d+(1.5 or 15 mg/kg), or h-rac (racemic mixture of protonated enantiomers h− and h+; 3 mg/kg). The compound h-rac was administered at twice the dose of the deuterated enantiomers since it contains 50% (i.e., 1.5 mg/kg) of each enantiomer. Body weight measurements were taken daily for the first week then biweekly. Tumor sizes were measured by caliper biweekly. The study was terminated after 23 days of dosing, then all animals were euthanized.

Figure 10:
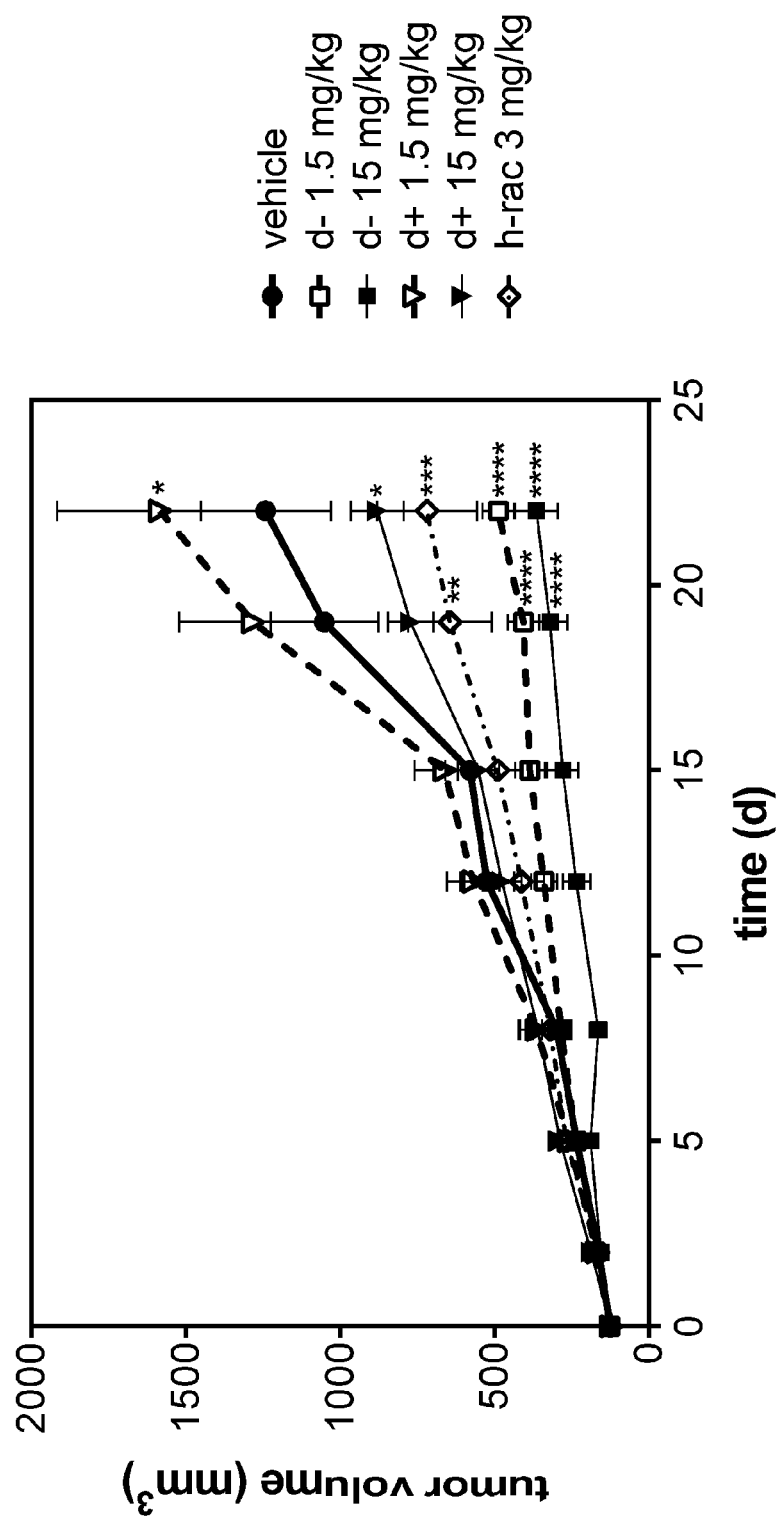
FIG. 10 is a graph showing average H929 xenograft tumor volume (±SEM) as a function of time in female CB.17 SCID mice treated daily by oral gavage with vehicle, racemic 3-(5-amino-2-methyl-4-oxoquinazolin-3(4H)-yl)-piperidine-2,6-dione (abbreviated "h-rac"), (+)-3-(5-amino-2-methyl-4-oxoquinazolin-3(4H)-yl)-(3-$^2$H)-piperidine-2,6-dione (abbreviated "d+"), or (−)-3-(5-amino-2-methyl-4-oxoquinazolin-3(4H)-yl)-(3-$^2$H)-piperidine-2,6-dione (abbreviated "d−"); where data were analyzed by 2-way ANOVA followed by post-hoc analysis using Bonferroni's test against vehicle group (* p<0.05,  p<0.01, * p<0.001, **** p<0.0001), as described in Example 5.

Tumor volume as a function of time is shown in FIG. 10. As the results in FIG. 10 show, deuterated enantiomer d− was more potent at limiting tumor growth at both doses than h− rac (i.e., the racemic mixture of compound not enriched in deuterium). The other deuterated enantiomer (i.e., d+) was less efficacious than d−, and efficacy for d+ was observed only at the highest dose of d+.

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise that as specifically described herein.

The invention claimed is:

1. A deuterium-enriched compound represented by:

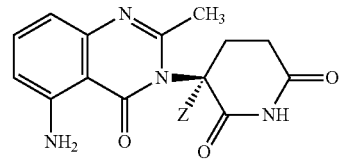

having an enantiomeric excess of at least 90%, or a pharmaceutically acceptable salt thereof; wherein:
Z is D.

2. The deuterium-enriched compound of claim 1, wherein the compound has an enantiomeric excess of at least 95%.

3. A pharmaceutical composition, comprising a pharmaceutically acceptable carrier and a compound of claim 1.

4. A pharmaceutical composition, comprising a pharmaceutically acceptable carrier and a compound of claim 2.

* * * * *